United States Patent
Pati et al.

(10) Patent No.: US 10,052,310 B2
(45) Date of Patent: Aug. 21, 2018

(54) SEPARASE INHIBITORS AND USES THEREOF

(71) Applicant: Baylor College of Medicine, Houston, TX (US)

(72) Inventors: Debananda Pati, Houston, TX (US); Nenggang Zhang, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 15/030,070

(22) PCT Filed: Oct. 20, 2014

(86) PCT No.: PCT/US2014/061353
§ 371 (c)(1),
(2) Date: Apr. 18, 2016

(87) PCT Pub. No.: WO2015/058185
PCT Pub. Date: Apr. 23, 2015

(65) Prior Publication Data
US 2016/0250191 A1  Sep. 1, 2016

Related U.S. Application Data

(60) Provisional application No. 61/892,911, filed on Oct. 18, 2013, provisional application No. 61/936,976, filed on Feb. 7, 2014.

(51) Int. Cl.
*A61K 31/4184* (2006.01)
*A61K 31/428* (2006.01)
*A61K 31/423* (2006.01)
*A61K 31/4245* (2006.01)

(52) U.S. Cl.
CPC ........ *A61K 31/4184* (2013.01); *A61K 31/423* (2013.01); *A61K 31/428* (2013.01); *A61K 31/4245* (2013.01)

(58) Field of Classification Search
CPC . A61K 31/4184; A61K 31/423; A61K 31/428
USPC ................................................ 514/303, 395
See application file for complete search history.

(56) References Cited

U.S. PATENT DOCUMENTS

| | | |
|---|---|---|
| 4,246,196 A | 1/1981 | Arndt et al. |
| 4,343,942 A | 8/1982 | Issidorides et al. |
| 5,435,860 A | 7/1995 | Maki et al. |
| 2002/0164620 A1* | 11/2002 | Peters ............... A61K 38/08 435/6.11 |
| 2009/0175873 A1 | 7/2009 | Liu |

OTHER PUBLICATIONS

Meyer et al, Clinical Cancer Research (2009), vol. 15(8), pp. 2703-2710.*

(Continued)

*Primary Examiner* — Craig D Ricci
*Assistant Examiner* — Janet L. Coppins
(74) *Attorney, Agent, or Firm* — Winstead PC

(57) ABSTRACT

In some embodiments, the present disclosure pertains to compositions with compounds that inhibit Separase activity. In additional embodiments, the present disclosure pertains to methods of treating a tumor in a subject by administering one or more compositions of the present disclosure to the subject.

19 Claims, 13 Drawing Sheets

(56) References Cited

OTHER PUBLICATIONS

Boriani et al, Eur J. Med. Chem. (2009), vol. 44, pp. 4426-4433.*
Samsonov, V.A., Russian J. Org. Chem. (2012), vol. 48, No. 3, pp. 399-410.*
Boriani et al, Eur J. Med. Chem. (2009), vol. 44, pp. 4426-4433. (Year: 2009).*
Samsonov, V.A., Russian J. Org. Chem. (2012), vol. 48, No. 3, pp. 399-410. (Year: 2012).*
International Preliminary Report on Patentability for PCT/US2014/061353, dated Apr. 28, 2016.
International Search Report and Written Opinion for PCT/US2014/061353, dated Dec. 24, 2014.
Meyer, et al. "Overexpression and Mislocalization of the Chrosmosomal Segregation Protein Separase in Multiple Human Cancers", Clin Cancer Res., 2009, vol. 15(8), pp. 2703-2710.
Zhang N, Ge G, Meyer R, Sethi S, Basu D, Pradhan S, et al. (2008). Overexpression of Separase induces aneuploidy and mammary tumorigenesis. Proc Natl Acad Sci U S A;105(35):13033-8.
Zhang N, Scorsone K, Ge G, Kaffes CC, Dobrolecki LE, Mukherjee M, Lewis MT, Berg S, Stephan CC and Pati D. (2014). Identification and characterization of Separase Inhibitors (Sepins) for Cancer Therapy. J. Biomolecular Screening 19(6): 878-889.
Pati, D. Oncogenic activity of separase. Cell Cycle 2008, 7, 3481-3482.
Hornig, N. C.; Knowles, P. P.; McDonald, N. Q.; et al. The dual mechanism of separase regulation by securin. Curr. Biol. 2002, 12, 973-982.
Gorr, I. H.; Boos, D.; Stemmann, O. Mutual inhibition of separase and Cdk1 by two-step complex formation. Mol. Cell 2005, 19, 135-141.
Basu, D.; Zhang, N.; Panigrahi, A. K.; et al. Development and validation of a fluorogenic assay to measure separase enzyme activity. Anal. Biochem. 2009, 392, 133-138.
Viadiu, H.; Stemmann, O.; Kirschner, M. W.; et al. Domain structure of separase and its binding to securin as determined by EM. Nat. Struct. Mol. Biol. 2005, 12, 552-553.
Sullivan, M.; Hornig, N. C.; Porstmann, T.; et al. Studies on substrate recognition by the budding yeast separase. J. Biol. Chem. 2004, 279, 1191-1196.
Mukherjee, M.; Ge, G.; Zhang, N.; et al. Separase loss of function cooperates with the loss of p53 in the initiation and progression of T- and B-cell lymphoma, leukemia and aneuploidy in mice. PLoS. ONE. 2011, 6, e22167.
Matsuo K, Ohsumi K, Iwabuchi M, Kawamata T, Ono Y, Takahashi M. (2012). Kendrin is a novel substrate for Separase involved in the licensing of centriole duplication. Curr Biol. 22(10):915-21.

* cited by examiner

C

D

E

SEPARASE INHIBITORS AND USES THEREOF

CROSS-REFERENCE TO RELATED APPLICATIONS

This application claims priority to U.S. Provisional Patent Application No. 61/892,911, filed on Oct. 18, 2013; and U.S. Provisional Patent Application No. 61/936,976, filed on Feb. 7, 2014. The entirety of each of the aforementioned applications is incorporated herein by reference.

STATEMENT REGARDING FEDERALLY SPONSORED RESEARCH

This invention was made with government support under Grant No. 1RO1 CA109330, awarded by the National Institutes of Health. The government has certain rights in the invention.

BACKGROUND

Currently, there is no method or composition to target human tumors with abnormal chromosome numbers (aneuploidy). Moreover, current methods and compositions for treating various types of tumors have limitations in terms of efficacy and specificity. Therefore, more effective compositions and methods are needed to address the above limitations, especially for tumors with aneuploidy.

SUMMARY

In some embodiments, the present disclosure pertains to compositions that inhibit Separase activity. In some embodiments, the compositions of the present disclosure include one or more compounds with one or more of the following structures:

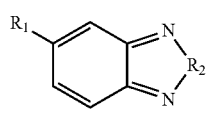
(1)

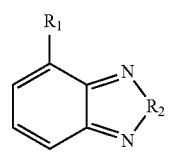
(2)

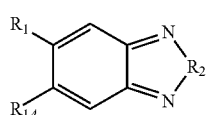
(3)

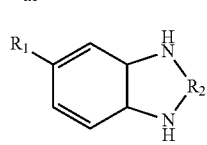
(4)

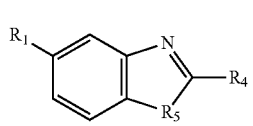
(5)

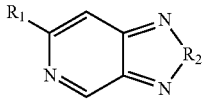
(6)

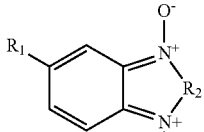
(7)

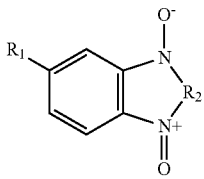
(8)

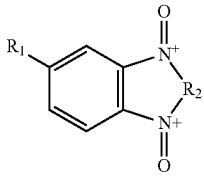
(9)

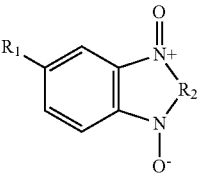
(10)

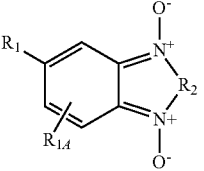
(11)

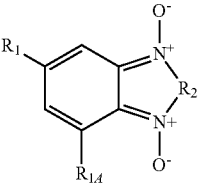
(12)

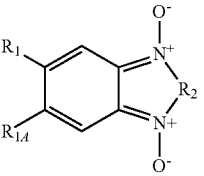
(13)

In some embodiments, $R_1$ (in structures 1-13) and $R_{1A}$ (in structures 3 and 11-13) are each selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, CH$_3$, CH$_3$O, CO$_2$H, CONH$_2$, CONHR$_3$, NHR$_3$, N(R$_3$)$_2$, C$_2$R$_3$, C$_4$H$_9$, phenyl, CH$_2$-phenyl, SO$_3$H, and combinations thereof. In some embodiments, R$_3$ (in structures 1-13) is selected from the group consisting of H, OH, CH$_3$, C$_4$H$_9$, alkyl groups, and combinations thereof. In some embodiments, R$_2$ (in structures 1-4 and 6-13) is selected from the group consisting of alkanes, C(CH$_3$)$_2$, cycloalkanes, cyclopentane, cyclohexane, phenyl, C(R$_7$)(R$_{7.5}$), C(CH$_3$)(R$_{7.5}$), C(CH$_3$)(CH$_2$CH$_3$), C(CH$_3$)(Phenyl), C(CH$_3$)(CF$_3$), C(C$_4$H$_9$)$_2$, CO, CS, CH$_2$, O, and combinations thereof. In some embodiments, R$_7$ and R$_{7.5}$ (in structures 1-4 and 6-13) are each selected from the group consisting of alkanes, CH$_3$, CH$_2$CH$_3$, cycloalkanes, cyclopentane, cyclohexane, phenyl, C$_4$H$_9$, CO, CS, and combinations thereof.

In some embodiments, R$_4$ (in structure 5) is selected from the group consisting of alkanes, cycloalkanes, cyclopentane, cyclohexane, CH$_3$, phenyl, O-phenyl, NH-phenyl, and combinations thereof. In some embodiments, R$_5$ (in structure 5) is selected from the group consisting of NH, NR$_6$, S, O, and combinations thereof. In some embodiments, R$_6$ (in structure 5) is selected from the group consisting of H, OH, CH$_3$, C$_4$H$_9$, alkyl groups, and combinations thereof.

In more specific embodiments, the compositions of the present disclosure include one or more compounds with the following structure:

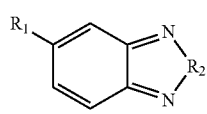

(1)

In some embodiments, R$_1$ in structure 1 is NO$_2$, and R$_2$ in structure 1 is C(CH$_3$)$_2$. In some embodiments, R$_1$ in structure 1 is Br and R$_2$ in structure 1 is CS.

In more specific embodiments, the compositions of the present disclosure include one or more compounds with the following structure:

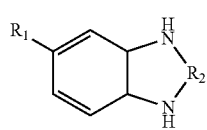

(4)

In some embodiments, R$_1$ in structure 4 is Br, and R$_2$ in structure 4 is CS.

In more specific embodiments, the compositions of the present disclosure include one or more compounds with the following structure:

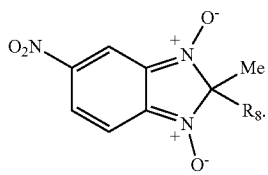

In some embodiments, R$_8$ is selected from the group consisting of alkanes, CH$_3$, CH$_2$CH$_3$, cycloalkanes, cyclopentane, cyclohexane, phenyl, C$_4$H$_9$, CO, CS, and combinations thereof.

In further embodiments, the compositions of the present disclosure include one or more compounds with the following structure:

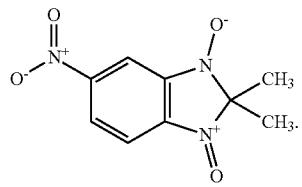 [SMILES: CC1(C)N([O-])c2cc([N+](=O)[O-])ccc2[N+]1=O]

In some embodiments, the compounds of the present disclosure are water soluble. In some embodiments, the compounds of the present disclosure are selective inhibitors of Separase. In some embodiments, the compounds of the present disclosure are non-competitive inhibitors of Separase.

In additional embodiments, the present disclosure pertains to methods of treating a tumor in a subject by administering one or more compositions of the present disclosure to the subject. In some embodiments, the tumor comprises Separase overexpressed tumor cells, such as Separase overexpressed mammary tumor cells or Separase overexpressed aneuploid cells.

In some embodiments, the tumor to be treated by the compositions of the present disclosure is associated with at least one of breast cancer, ovarian cancer, leukemia, thyroid cancer, neuroblastoma, brain cancer, lung cancer, colon cancer, gastrointestinal cancer, prostate cancer, osteosarcoma, glioblastoma, and combinations thereof. In some embodiments, the tumor to be treated by the compositions of the present disclosure is associated with breast cancer, such as triple negative breast cancer and luminal-B subtype endocrine resistant breast cancer.

In some embodiments, the subjects to be treated by the compositions of the present disclosure are human beings, such as human beings suffering from cancer. In some embodiments, the compositions of the present disclosure are administered to subjects by intravenous administration.

DESCRIPTION OF THE FIGURES

FIG. 1A provides structures of 2,2-dimethyl-5-nitro-2H-benzimidazole trihydrate (left panel), SYC-764 (center), and SYC-763 (right panel). FIGS. 1B-C provides structures of various derivatives of the compounds in FIG. 1A. FIG. 1D provides the structure of Sepin-1. FIG. 1E provides structures of various Sepin-1 derivatives.

FIG. 2A shows a Rh110 standard curve. The fluorescence intensity expressed by the relative fluorescent units (RFU) is linearly proportional to the amount of Rh110, which can be used to determine the amount of Rh110 formation in Separase assay. FIG. 2B shows that the amount of free Rh110 released from (Rad21)2-Rh110 is a function of the substrate concentration. The amount of Separase used in this experiment was 5 ng/well. FIG. 2C shows the amount of free Rh110 released from (Rad21)2-Rh110 was correlated to the amount of Separase enzyme concentration. The amount of Rh110 used in this experiment was 1 nmol/well. FIG. 2D shows optimization of incubation time for the fluorogenic Separase assay. After Separase and (Rad21)2-Rh110 were mixed, the reaction mixtures were incubated at 25° C. or 37° C. The fluorescence intensity was determined every 30 min. Bar=mean of 3 samples±SD. pmol Rh110/h on the second y-axis in FIGS. 2B and 2C was calculated using the standard curve shown in FIG. 2A.

FIG. 4A shows aliquots of diluted Separase in working concentration were kept on ice for 8 h and then stored at −80, −20 or 4° C. for 24 h. Their activity was analyzed in comparison to the same concentration of Separase that was freshly prepared from stock solutions. FIG. 4B shows diluted (Rad21)2-Rh110 in working concentration was stored at −80 or 4° C. for 24 h. The activity was analyzed using Separase assay. The same concentration of (Rad21)2-Rh110 that was freshly prepared from stock solution was used as control. FIG. 4C shows results where TEV protease and Separase were used to hydrolyze (Rad21)2-Rh110. The enzyme activity was determined after incubation at 37° C. for 3 h. FIG. 4D shows the effect of DMSO concentration on Separase assay.

FIG. 5A shows the reproducibility of the screening. Each data point was repeated in two plates (A and B) and plotted with the Separase activity of A plate as x-axis and that of B plate as y-axis. A total of 9 representative duplicated 384-well plates with 3,456 data points are shown. FIG. 5B shows RFU of Positive controls is well separated from that of the negative controls. 576 data points of positive controls and negative controls, respectively, from 18 384-well plates are shown. σ is STDEV. FIG. 5C is a chart summarizing the robustness of high throughput screening (HTS). 14,400 compounds in 180 96-well plates were screened using 384-well plates in duplicates (A and B), with a total of 90 384-well plates. The value of signal to background ratio (S:B), signal to noise ratio (S:N) and the Z' factor is the mean of 90 plates, while the value of S:B range (A:B), S:N range (A:B) and Z' range (A:B) is the mean of 45 A plates or B plates. FIG. 5D shows results demonstrating the inhibition of Separase activity by the test compounds. The test compounds that inhibited at least 50% of Separase activity in both A plates and B plates were identified. The data points in the two upper right boxes showed the compounds that inhibited Separase activity by >50% and >80%, respectively. FIG. 5E illustrates that, among the 14,400 compounds assayed, 97 are found to inhibit Separase activity by >50%. The hit rate is 0.67%. 24 out of the 97 compounds inhibit Separase activity by >80%. Five of the 97 compounds were confirmed.

FIG. 6A provides a structure of Sepin-1. FIG. 6B shows that Sepin-1 inhibits the cleavage of Separase substrate Rad21. The in vitro transcribed and translated Myc-Rad21 was used as the substrate for activated Separase in the presence of or without Sepin-1. The final concentration of Sepin-1 in the reaction mixture was 50 µm. ($K_d$=molecular weight). FIG. 6C shows the inhibition of Separase activity by Sepin-1. The $IC_{50}$ was 14.8 µM, calculated using the KaleidaGraph program. The Inset shows a four-parameter dose-response curve fit with an estimated $IC_{50}$ of 15.8 µM. (n=3±SE). FIG. 6D shows the non-competitive inhibition Separase enzymatic activity by Sepin-1. Sepin-1 and Separase were mixed 30 min before substrate (Rad21)2-Rh110 was added. After 3 h incubation, the fluorescence intensity of Rh110 was determined. The data were shown in Lineweaver-Burt plot. Sepin-1 reduced the speed ($V_{max}$) of substrate conversion by Separase, but not the $K_m$.

FIG. 7A shows an immunoblot of the Separase protein in breast cancer cell lines, MCF7 and MCF10f. FIG. 7B shows results of an MTT assay where MCF7 is more sensitive to Sepin-1 in inhibiting cell growth than MCF10f ex vivo. FIG. 7C shows that Sepin-1 inhibits the growth of xenograft tumor derived from MCF-7 in SCID-beige mice. FIG. 7D shows the immunostaining of Separase in triple negative breast cancer tumor xenografts MC1 and BCM-5471. Tumor sections were stained with Separase mAb (green) and Ki67 pAb (red). DNA was stained with DAPI (blue). FIGS. 7E-F shows results where Sepin-1 inhibits the growth of xenograft tumors derived from breast cancer tumors in SCID-beige mice. BCM-5471 xenograft tumors are more sensitive to Sepin-1 than MC-1 tumors. The xenograft tumors' weight was assessed over three week period of Sepin-1 or vehicle treatment in SCID-beige mice at a dose of 10 mg/kg daily via intraperitoneal injection for 5 days a week (N=5/group). FIGS. 7G-H shows that Sepin-1-treated MCF-7 xenograft tumors have high level of apoptosis. Tumor sections from MCF-7 xenografts treated with Sepin-1 or vehicle were stained with H&E (FIG. 7G) or immunostained with cleaved caspase-3 mAb (FIG. 7H). Apoptotic bodies in H&E staining (black arrows) and immunostaining (green) were observed in Sepin-1-treated tumors.

FIGS. 8A-C shows that Sepin-1 inhibits cell growth of leukemia cell lines (FIG. 8A), breast cancer cell lines (FIG. 8B), and Neuroblastoma cell lines (FIG. 8C). Cells were treated with serially diluted Sepin-1 for 72 h. The cell viability was assessed using MTT assay. FIG. 8D shows a western blot of full length (FL) and N-terminal (NT, surrogate for the active protein) Separase in cancer cell lines. FIG. 8E shows a positive correlation between Separase protein level and sensitivity to Sepin-1 in inhibiting cell growth ($IC_{50}$). The Separase bands from (D) were quantified and normalized with beta actin. FIG. 8F shows immunoblotting shown Sepin-1-induced activation of caspase-3 and cleavage of poly (ADP-ribose) polymerase (Parp). Molt4 cells were treated with various concentrations of Sepin-1 for 24 h. Etoposide (Etop) was used as a control. Cl Parp refers to cleaved Parp. Cl Casp-3 refers to cleaved Caspase-3. * indicates non-specific bands.

FIG. 9A provides structures of the 5 lead compounds. FIG. 9B provides dose-dependent inhibition of Separase activity by Sepin 1 and 2.

FIG. 11A shows the structures of Sepin-1 derivatives that were tested. FIG. 11B shows data relating to the separase inhibition activities of the Sepin-1 derivatives. The numbers (28-31 in FIG. 11B) correspond to structures shown in FIG. 11A.

DETAILED DESCRIPTION

Figure 1:
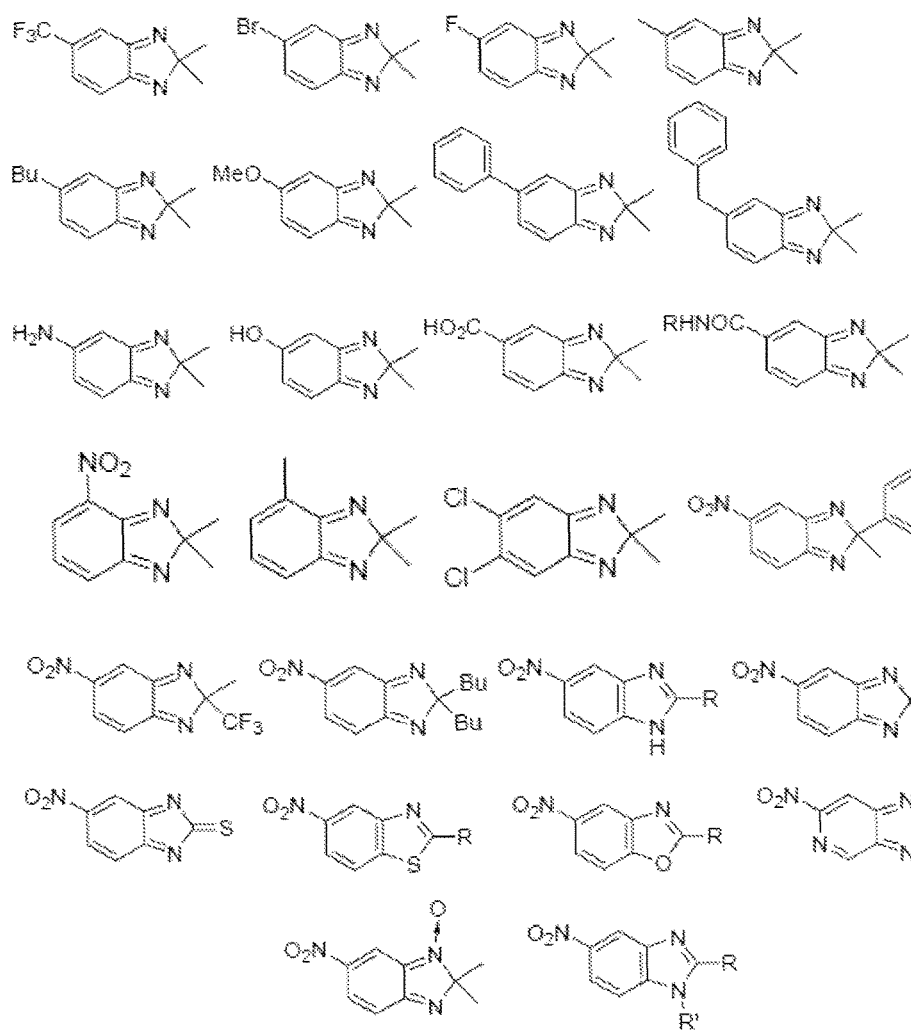
FIG. 1 provides structures of various separase inhibitors and potential separase inhibitors.
Figure 1:
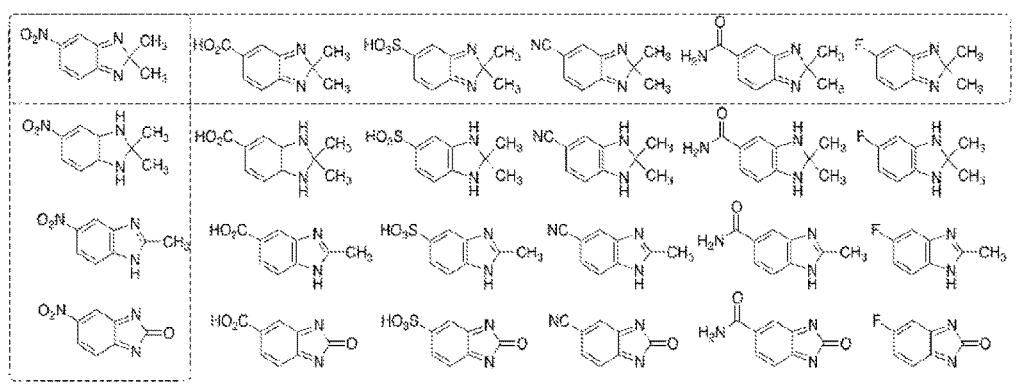
Figure 1:
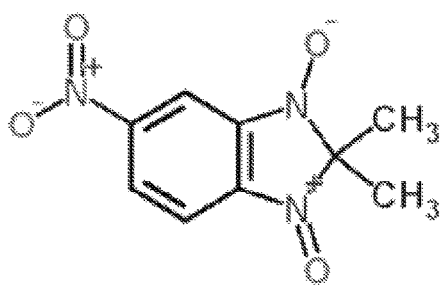
Figure 1:
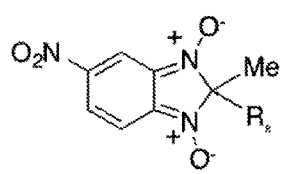
Figure 1:
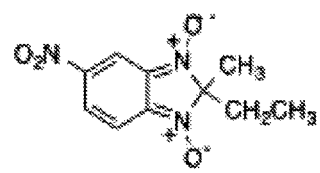
Figure 1:
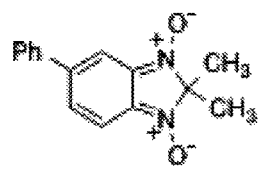
Figure 1:
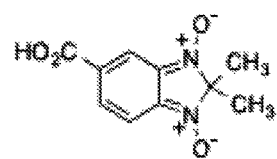
Figure 1:
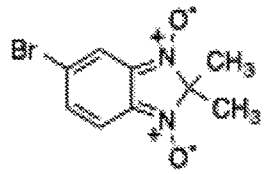
Figure 1:
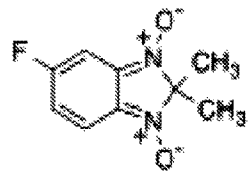
Figure 1:
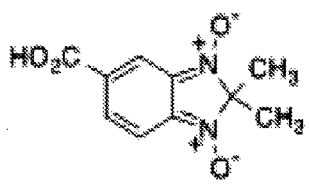
Figure 1:
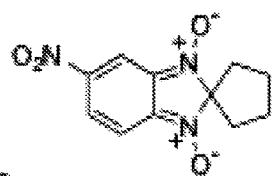
Figure 1:
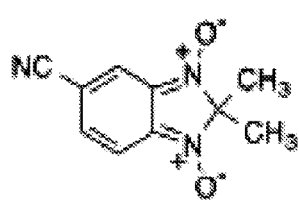

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Separase is a protease evolutionarily conserved from yeast to human. Its primary function is to cleave the cohesin subunit Scc1/Mcd1/Rad21 at the onset of anaphase, resulting in the dissolution of cohesin rings and independent segregation of sister chromatids into the two daughter cells.

Recent studies indicate that Separase is overexpressed and mislocalized in a number of human tumors, including breast, prostate and osteosarcoma. In fact, Separase overexpression is reported in a broad range of human tumors. In addition, Separase overexpression in mouse models results in tumorigenesis. Furthermore, Separase is significantly overexpressed in over 60% of human breast tumors compared to the matched normal breast tissue. In addition, the conditional overexpression of Separase in mammary epithelial cells is sufficient to induce separation of sister chromatids, aneuploidy and tumorigenesis. These data suggest that abnormal Separase expression and mislocalization is a driver of aneuploidy and tumorigenesis.

Separase activity is tightly regulated during the cell cycle and is inactive when it binds to its inhibitory chaperone, securin. Separase is also inhibited via phosphorylation at Ser1126 by Cyclin B-Cdk1 kinase and binding to Cyclin B. With the progression of cell cycle to the onset of anaphase, the anaphase promoting complex/cyclosome polyubiquitinates mitotic cyclin and securin, which are rapidly degraded by the 26S proteasome. Once enzymatically activated, Separase auto-cleaves, resulting in N-terminal and C-terminal fragments, which still associate with each other. The main function of Separase is to proteolytically cleave the cohesin subunit Rad21.

Because Separase is overexpressed in human tumors, and its overexpression results in chromosomal missegregation and aneuploidy, pharmacological inhibition of Separase presents a novel strategy to target chromosomal missegregation induced tumorigenesis. Pharmacologic modulation of Separase activity remains elusive, however, due to a lack of small molecular compound inhibitors.

In some embodiments, the present disclosure pertains to compositions that inhibit Separase activity. In some embodiments, the present disclosure pertains to methods of treating a tumor in a subject by administering the compositions of the present disclosure to the subject.

Compositions

In some embodiments, the compositions of the present disclosure include one or more compounds that inhibit Separase activity. In some embodiments, the compounds include one or more of the following structures:

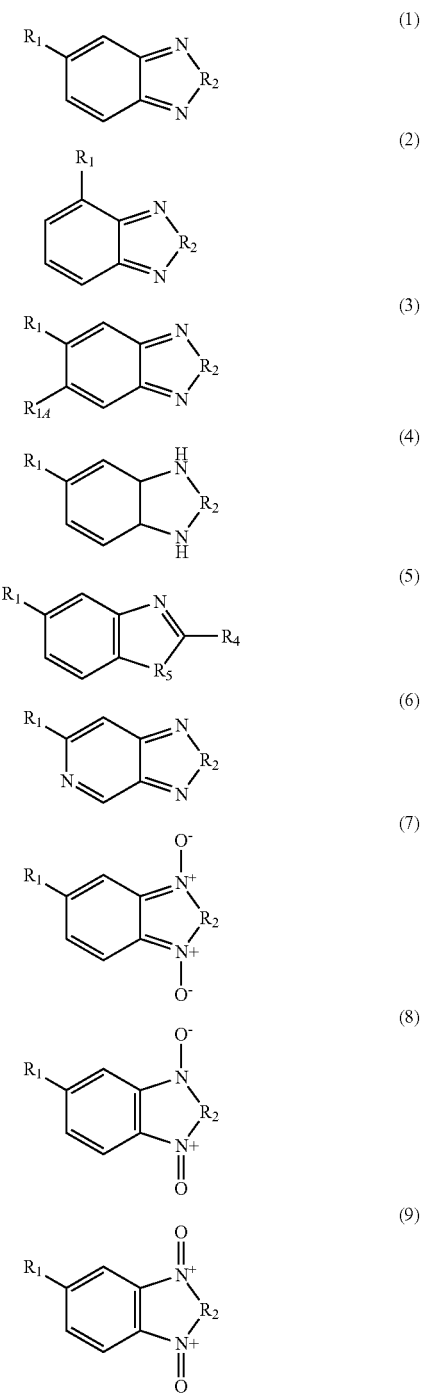

-continued

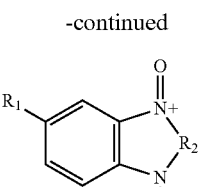

(10)

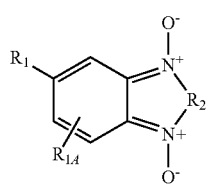

(11)

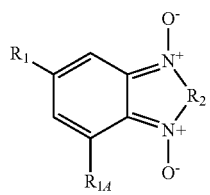

(12)

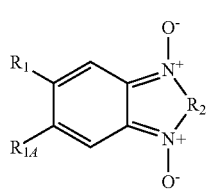

(13)

One skilled in the art will recognize that the above structures can represent numerous different compounds. Exemplary compounds represented by the above structures are illustrated in FIGS. 1A-E.

One skilled in the art will also recognize that structures 1-13 can resonate in different manners. For instance, in some embodiments, structures 7-10 may represent different resonating structures of the same compounds. Likewise, in some embodiments, structures 11-13 may resonate to resemble the compounds disclosed in structures 7-10. Therefore, various embodiments of the present disclosure also cover resonating versions of structures 1-13 that may not be disclosed in the aforementioned structures.

Additional compounds that represent variations of the above structures can also be envisioned. For instance, in some embodiments, $R_1$ (in structures 1-13) and $R_{1A}$ (in structures 3 and 11-13) are each selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, phenyl, $CH_2$-phenyl, $SO_3H$, and combinations thereof. In some embodiments $R_1$ (in structures 1-13) is $NO_2$. In some embodiments, $R_1$ and $R_{1A}$ (in structures 3 and 11-13) are Cl. In some embodiments, $R_1$ (in structures 1-13) is $NO_2$, and $R_{1A}$ (in structures 3 and 11-13) is Br.

In some embodiments, $R_3$ (in structures 1-13) is selected from the group consisting of H, OH, $CH_3$, $C_4H_9$, alkyl groups, and combinations thereof. In some embodiments, $R_3$ (in structures 1-13) is H.

In some embodiments, $R_2$ (in structures 1-4 and 6-13) is selected from the group consisting of alkanes, $C(CH_3)_2$, cycloalkanes, cyclopentane, cyclohexane, phenyl, $C(R_7)(R_{7.5})$, $C(CH_3)(R_{7.5})$, $C(CH_3)(CH_2CH_3)$, $C(CH_3)(Phenyl)$, $C(CH_3)(CF_3)$, $C(C_4H_9)_2$, CO, CS, $CH_2$, O, and combinations thereof. In some embodiments, $R_7$ and $R_{7.5}$ (in structures 1-4 and 6-13) are each selected from the group consisting of alkanes, $CH_3$, $CH_2CH_3$, cycloalkanes, cyclopentane, cyclohexane, phenyl, $C_4H_9$, CO, CS, and combinations thereof. In some embodiments, $R_2$ (in structures 1-4 and 6-13) is $C(CH_3)_2$.

In some embodiments, $R_4$ (in structure 5) is selected from the group consisting of alkanes, cycloalkanes, cyclopentane, cyclohexane, $CH_3$, phenyl, O-phenyl, NH-phenyl, and combinations thereof. In some embodiments, $R_4$ (in structure 5) is $CH_3$.

In some embodiments, $R_5$ (in structure 5) is selected from the group consisting of NH, $NR_6$, S, O, and combinations thereof. In some embodiments, $R_5$ (in structure 5) is NH. In some embodiments, $R_6$ (in structure 5) is selected from the group consisting of H, OH, $CH_3$, $C_4H_9$, alkyl groups, and combinations thereof.

In more specific embodiments, the compositions of the present disclosure include one or more compounds with the following structure:

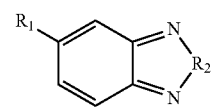

(1)

In some embodiments, $R_1$ in structure 1 is selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, phenyl, $CH_2$-phenyl, $SO_3H$, and combinations thereof. In some embodiments, $R_3$ in structure 1 is selected from the group consisting of H, OH, $CH_3$, $C_4H_9$, alkyl groups, and combinations thereof. In some embodiments, $R_3$ in structure 1 is H. In some embodiments, $R_2$ in structure 1 is selected from the group consisting of alkanes, $C(CH_3)_2$, cycloalkanes, cyclopentane, cyclohexane, phenyl, $C(R_7)(R_{7.5})$, $C(CH_3)(R_{7.5})$, $C(CH_3)(CH_2CH_3)$, $C(CH_3)(Phenyl)$, $C(CH_3)(CF_3)$, $C(C_4H_9)_2$, CO, CS, $CH_2$, O, and combinations thereof. In some embodiments, $R_7$ and $R_{7.5}$ are each selected from the group consisting of alkanes, $CH_3$, $CH_2CH_3$, cycloalkanes, cyclopentane, cyclohexane, phenyl, $C_4H_9$, CO, CS, and combinations thereof. In some embodiments illustrated in FIG. 1A (left panel), $R_1$ in structure 1 is $NO_2$, and $R_2$ in structure 1 is $C(CH_3)_2$. In some embodiments illustrated in FIG. 1A (middle panel), $R_1$ in structure 1 is Br, and $R_2$ in structure 1 is CS.

In more specific embodiments, the compositions of the present disclosure include one or more compounds with the following structure:

(4)

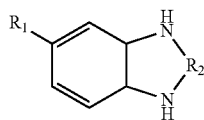

In some embodiments, $R_1$ in structure 4 is selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, phenyl, $CH_2$-phenyl, $SO_3H$, and combinations thereof. In some embodiments, $R_3$ in structure 4 is selected from the group consisting of H, OH, $CH_3$, $C_4H_9$, alkyl groups, and combinations thereof. In some embodiments, $R_3$ in structure 4 is H. In some embodiments, $R_2$ in structure 4 is selected from the group consisting of alkanes, $C(CH_3)_2$, cycloalkanes, cyclopentane, cyclohexane, phenyl, $C(R_7)(R_{7.5})$, $C(CH_3)(R_{7.5})$, $C(CH_3)(CH_2CH_3)$, $C(CH_3)$(Phenyl), $C(CH_3)(CF_3)$, $C(C_4H_9)_2$, CO, CS, $CH_2$, O, and combinations thereof. In some embodiments, $R_7$ and $R_{7.5}$ are each selected from the group consisting of alkanes, $CH_3$, $CH_2CH_3$, cycloalkanes, cyclopentane, cyclohexane, phenyl, $C_4H_9$, CO, CS, and combinations thereof. In some embodiments illustrated in FIG. 1A (right panel), $R_1$ in structure 4 is Br, and $R_2$ in structure 4 is CS.

In more specific embodiments, the compositions of the present disclosure include one or more compounds with one or more of the following structures:

(7)

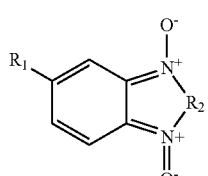

(8)

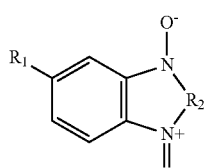

(9)

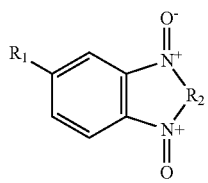

(10)

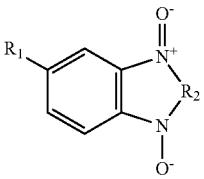

(11)

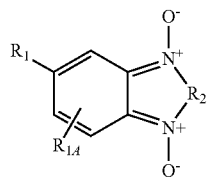

(12)

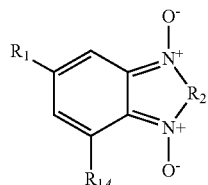

(13)

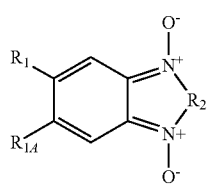

In some embodiments, $R_1$ (in structures 7-13) and $R_{1A}$ (in structures 11-13) are each selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, phenyl, $CH_2$-phenyl, $SO_3H$, and combinations thereof. In some embodiments, $R_3$ (in structures 7-13) is selected from the group consisting of H, OH, $CH_3$, $C_4H_9$, alkyl groups, and combinations thereof. In some embodiments, $R_2$ (in structures 7-13) is selected from the group consisting of alkanes, $C(CH_3)_2$, cycloalkanes, cyclopentane, cyclohexane, phenyl, $C(R_7)(R_{7.5})$, $C(CH_3)(R_{7.5})$, $C(CH_3)(CH_2CH_3)$, $C(CH_3)$(Phenyl), $C(CH_3)(CF_3)$, $C(C_4H_9)_2$, CO, CS, $CH_2$, O, and combinations thereof. In some embodiments, $R_7$ and $R_{7.5}$ (in structures 7-13) are each selected from the group consisting of alkanes, $CH_3$, $CH_2CH_3$, cycloalkanes, cyclopentane, cyclohexane, phenyl, $C_4H_9$, CO, CS, and combinations thereof.

In more specific embodiments, the compositions of the present disclosure include one or more compounds with the following structure:

(12)

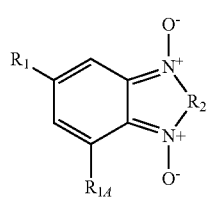

In some embodiments, $R_1$ and $R_{1A}$ in are each selected from the group consisting of alkanes, alkenes, alkynes, carboxyl groups, alkoxy groups, methoxy groups, ethers, nitro groups, nitriles, sulfates, sulfonates, halogens, primary amine groups, secondary amine groups, tertiary amine groups, alcohols, boronic acids, triazoles, photo-reactive groups, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, phenyl, $CH_2$-phenyl, $SO_3H$, and combinations thereof. In some embodiments, $R_3$ in structure 12 is selected from the group consisting of H, OH, $CH_3$, $C_4H_9$, alkyl groups, and combinations thereof. In some embodiments, $R_3$ in structure 12 is H. In some embodiments, $R_2$ in structure 12 is selected from the group consisting of alkanes, $C(CH_3)_2$, cycloalkanes, cyclopentane, cyclohexane, phenyl, $C(R_7)(R_{7.5})$, $C(CH_3)(R_{7.5})$, $C(CH_3)(CH_2CH_3)$, $C(CH_3)$(Phenyl), $C(CH_3)(CF_3)$, $C(C_4H_9)_2$, CO, CS, $CH_2$, O, and combinations thereof. In some embodiments, $R_7$ and $R_{7.5}$ are each selected from the group consisting of alkanes, $CH_3$, $CH_2CH_3$, cycloalkanes, cyclopentane, cyclohexane, phenyl, $C_4H_9$, CO, CS, and combinations thereof. In some embodiments, $R_1$ in structure 12 is $NO_2$, $R_{1.4}$ in structure 12 is Br, and $R_2$ in structure 12 is $C(CH_3)_2$.

In further embodiments, the compositions of the present disclosure include one or more compounds with the following structure:

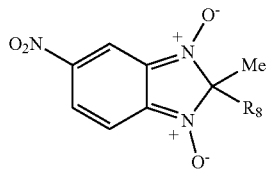

In some embodiments, $R_8$ is selected from the group consisting of alkanes, $CH_3$, $CH_2CH_3$, cycloalkanes, cyclopentane, cyclohexane, phenyl, $C_4H_9$, CO, CS, and combinations thereof.

In more specific embodiments, the compositions of the present disclosure include one or more compounds with the following structure (referred to as Sepin-1 and also shown in FIG. 1D):

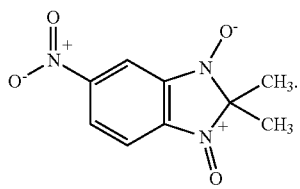

In more specific embodiments, the compositions of the present disclosure include one or more derivatives of Sepin-1. In some embodiments, the Sepin-1 derivatives include, without limitation, one or more of the structures shown in FIG. 1E.

Composition Content

In various embodiments, the compositions of the present disclosure can contain one or more of the aforementioned compounds that inhibit Separase activity. In some embodiments, the compositions of the present disclosure can also have one or more physiologically acceptable carriers or excipients. In some embodiments, the compositions of the present disclosure can also include formulation materials for modifying, maintaining, or preserving various conditions, including pH, osmolarity, viscosity, clarity, color, isotonicity, odor, sterility, stability, rate of dissolution or release, and/or adsorption or penetration of the compounds. Suitable formulation materials include, but are not limited to: amino acids (e.g., glycine); antimicrobials; antioxidants (e.g., ascorbic acid); buffers (e.g., Tris-HCl); bulking agents (e.g., mannitol and glycine); chelating agents (e.g., EDTA); complexing agents (e.g., hydroxypropyl-beta-cyclodextrin); and the like.

Compound Properties

The compounds in the compositions of the present disclosure can have various properties. For instance, in some embodiments, the compounds of the present disclosure are water soluble. In some embodiments, the compounds of the present disclosure inhibit Separase activity. In some embodiments, the compounds of the present disclosure are non-competitive inhibitors of Separase.

In more specific embodiments, the compounds of the present disclosure are selective inhibitors of Separase. For instance, in some embodiments, the compounds of the present disclosure inhibit Separase activity without significantly inhibiting the activity of other enzymes. In more specific embodiments, the compounds of the present disclosure inhibit Separase activity without significantly inhibiting the activity of cysteine proteases other than Separase (e.g., Caspases, tissue kallikrein, coagulation factor Xa, and other proteases that cleave after arginine at P1 position).

In some embodiments, the compounds of the present disclosure inhibit the growth of tumor cells. For instance, in some embodiments, the compounds of the present disclosure can inhibit the growth of Separase overexpressed tumor cells. In some embodiments, the compounds of the present disclosure can selectively inhibit the growth of Separase overexpressed tumor cells without significantly affecting the growth of normal cells. In some embodiments, the compounds of the present disclosure can selectively inhibit the growth of Separase overexpressed aneuploid cells.

In some embodiments, the compounds of the present disclosure inhibit the growth of tumor cells at $IC_{50}$ concentrations that range from about 0.5 µm to about 65 µm. In some embodiments, the compounds of the present disclosure inhibit the growth of tumor cells at $IC_{50}$ concentrations that range from about 1 µm to about 10 µm.

Methods of Treating Tumors

In view of the above properties, the compounds of the present disclosure can have numerous applications in treating tumors. As such, additional embodiments of the present disclosure pertain to methods of treating various tumors in various subjects by administering one or more compositions of the present disclosure to the subject.

Tumors

The compositions of the present disclosure can be utilized to treat various types of tumors. For instance, in some embodiments, the tumors to be treated include Separase overexpressed tumor cells. In more specific embodiments, the tumors to be treated include Separase overexpressed mammary tumor cells, Separase overexpressed aneuploid cells, and combinations thereof.

In some embodiments, the tumors to be treated by the compositions of the present disclosure may be associated with various types of cancers. For instance, in some embodiments, the tumors to be treated may be associated with at least one of breast cancer, leukemia, thyroid cancer, neuroblastoma, brain cancer, lung cancer, colon cancer, prostate cancer, osteosarcoma, glioblastoma, ovarian cancer, gastrointestinal cancer and combinations thereof. In some embodiments, the tumors to be treated are associated with breast cancer. In some embodiments, the tumors to be treated are associated with triple negative breast cancer and luminal-B subtype endocrine resistant breast cancer.

Without being bound by theory, the compositions of the present disclosure can treat tumors by various mechanisms. For instance, in some embodiments, the compounds in the compositions of the present disclosure inhibit the growth of tumor cells associated with a tumor. In some embodiments, the compounds in the compositions of the present disclosure selectively inhibit the growth of Separase overexpressed tumor cells associated with the tumor. In some embodiments, the compounds in the compositions of the present disclosure selectively inhibit the growth of Separase overexpressed aneuploid cells associated with the tumor.

Subjects

The compositions of the present disclosure can be used to treat tumors in various subjects. For instance, in some embodiments, the subject is a human being. In some embodiments, the subject is a human being suffering from cancer. In additional embodiments, the subjects may be non-human animals, such as mice, rats, other rodents, or larger mammals, such as dogs, monkeys, pigs, cattle and horses.

Administration

The compositions of the present disclosure can be administered to subjects by various methods. For instance, the compositions of the present disclosure can be administered by oral administration (including gavage), inhalation, subcutaneous administration (sub-q), intravenous administration (I.V.), intraperitoneal administration (I.P.), intramuscular administration (I.M.), intrathecal injection, and combinations of such modes. In further embodiments, the therapeutic compositions of the present disclosure can be administered by topical application (e.g, transderm, ointments, creams, salves, eye drops, and the like). In more specific embodiments, the compositions of the present disclosure can be administered intravenously. Additional modes of administration can also be envisioned.

In various embodiments, the compositions of the present disclosure may also be administered in a single dose or multiple doses throughout a time period. For instance, in some embodiments, the compositions of the present disclosure may be administered to a subject in two separate doses.

In addition, the compositions of the present disclosure may be administered to localized sites in a subject, such as tissue or vasculature that contain a tumor. For instance, the compositions of the present disclosure may be injected directly into an area of a subject that displays tumor growth.

In various embodiments, the compositions of the present disclosure may be co-administered with other therapies. For instance, in some embodiments, the compositions of the present disclosure may be co-administered along with anti-cancer drugs.

ADDITIONAL EMBODIMENTS

Reference will now be made to more specific embodiments of the present disclosure and experimental results that provide support for such embodiments. However, Applicants note that the disclosure herein is for illustrative purposes only and is not intended to limit the scope of the claimed subject matter in any way.

Example 1. Identification and Characterization of Separase Inhibitors (Sepins) for Cancer Therapy In this Example, Applicants report a high throughput screening for Separase inhibitors (Sepins). Applicants developed a fluorogenic Separase assay using Rhodamine 110 conjugated Rad21 peptide as substrate and screened a small molecule compound library. In particular, Applicants have screened a chemical library with 14,400 small compounds and identified five compounds that inhibited Separase activity. Applicants have further characterized Sepin-1, a non-competitive inhibitor of Separase, which can inhibit the growth of cancer cell lines and mammary xenograft tumors in mice by inducing apoptosis. In particular, Applicants have observed that Sepin-1 inhibits Separase enzymatic activity with an $IC_{50}$ of 14.8 µM. Applicants have also found that the sensitivity to Sepin-1 in most cases is positively correlated to the level of Separase in both cancer cell lines and tumors.

Example 1.1. Development of Separase Activity Assay Using (Rad21)2-Rh110 as a Substrate 7-amido-4-methyl coumaric acid (AMC) is a commonly used dye in protease assays, and Applicants previously reported a fluorogenic Separase assay using AMC-labeled Rad21 peptide as the substrate (Anal. Biochem., 2009, 392, 133-138). One of the caveats of AMC-based protease assays is that the results from such assays can potentially be biased and misinterpreted due to the interference of label and compound auto fluorescence at the excitation and emission wavelength of 350 nm and 500 nm, respectively. These interfering factors can be significantly reduced by using redshift dyes, such as Rhodamine 110 (Rh110), which has been widely used in various protease assays.

Rad21 peptide (Asp-Arg-Glu-Ile-Nle-Arg) that contains Separase cleaving consensus motif (Glu-X-X-Arg) was conjugated to Rh110. Two Rad21 peptides were linked to one Rh110 molecule forming a bisamide, and the product was named (Rad21)2-Rh110.

Figure 2:
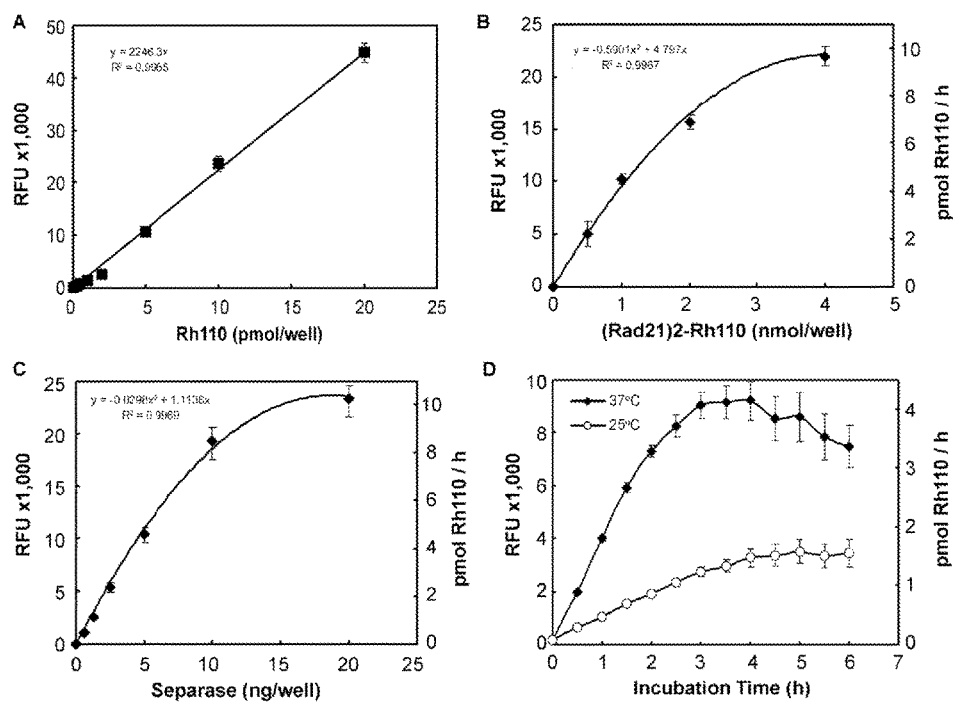
FIG. 2 provides data relating to the development of a fluorogenic Separase assay using (Rad21)2-Rh110 as a substrate.

Because the fluorophore is in the lactone state, (Rad21)2-Rh110 virtually has no autofluorescence. Once the amide bonds between the Rad21 peptide and Rh110 moiety is cleaved by Separase, the Rah110 moiety in the Rad21-Rh110 switches its lactone state to a quinine state, which exhibits significant increase of fluorescence intensity. The fluorescence intensity (relative fluorescence unit, RFU) increases proportionally with the increase of the amount of free Rh110, measured at $\lambda_{ex}$=490 nm and $\lambda_{em}$=528 nm (FIG. 2A). The standard curve of RFU versus Rh110 can be used to calculate the amount of Rh110 formed during the Separase assay.

Applicants tested the relationship of the increasing concentrations of substrate and enzyme combinations. The amount of Rh110 released was linearly correlated with the increase of (Rad21)2-Rh110 concentration between 0-2 nmol/well (FIG. 2B). Similarly, the amount of Rh110 released was a linear function with the increase of Separase concentration between 0-10 ng/well (FIG. 2C).

In addition, incubation temperature significantly affects the kinetics of Separase. The release of Rh110 catalyzed by Separase was much faster at 37° C. than that at room temperature (25° C.) (FIG. 2D). The amount of Rh110 released from (Rad21)2-Rh110 linearly increased between 0 and 3 h (FIG. 2D). Both di- and mono-substituted Rad21-Rh110 can be cleaved by Separase. The fluorescence intensity of mono-substituted Rad21-Rh110 is about 10% of free Rh110. Taking the assay efficiency and the cost effectiveness into consideration, Applicants developed the Separase assay using 5 ng (~21.7 fmol) of Separase and 1 nmol of (Rad21)2-Rh110 in 25 µl reaction volume with 3 h incubation at 37° C. This assay condition was adapted for the high throughput screening for Separase inhibitors that is described below.

Example 1.2. Kinetics of Hydrolysis of (Rad21)2-Rh110 by Separase

Figure 3:
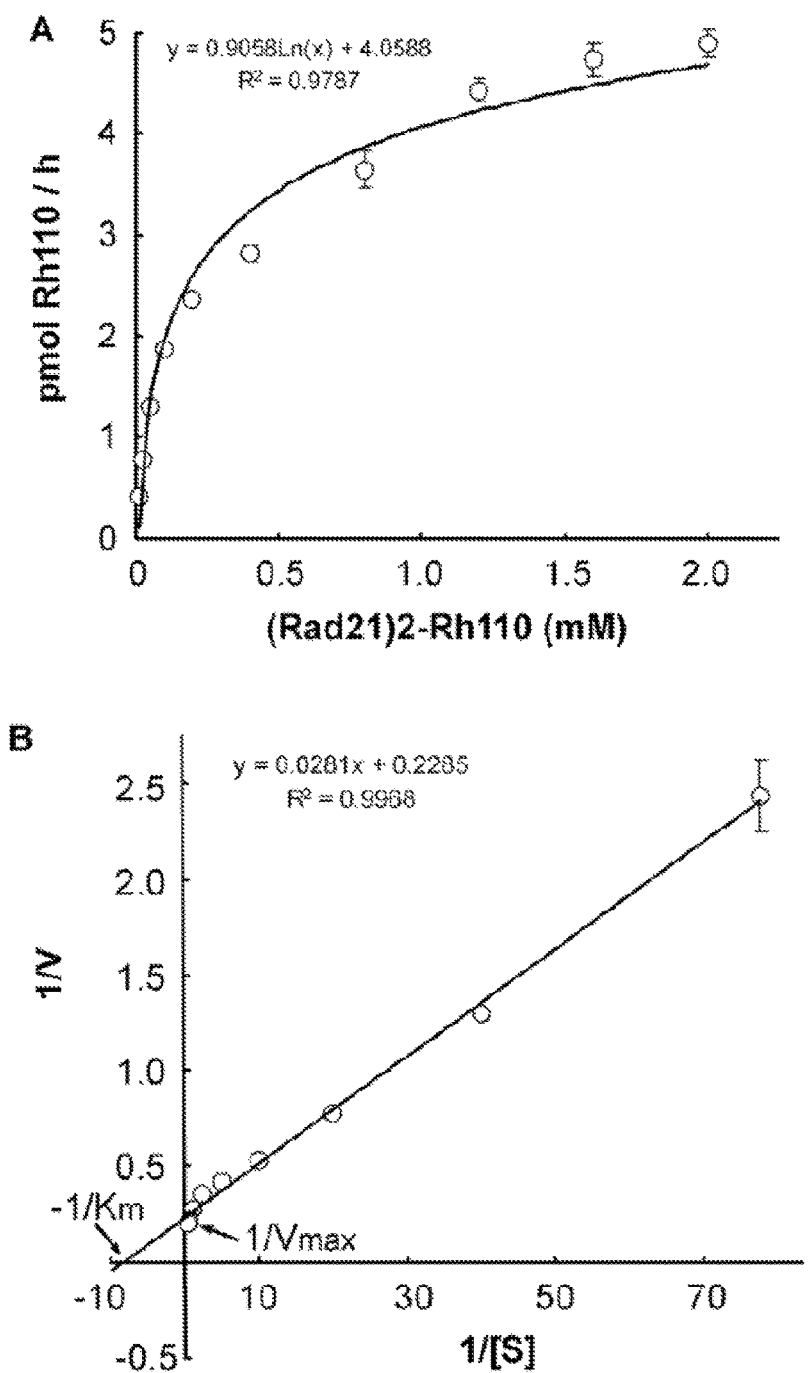
FIG. 3 shows results relating to the kinetics of the Separase assay. The cleavage reaction was carried out in the presence of the increased concentration (0.015-2 mM) of (Rad21)2-Rh110 and 5 ng of Separase. The total reaction volume was 25 µl. The plates were incubated at 37° C. for 3 h before the fluorescence intensity was determined. The fluorescence intensity was converted to pmol of Rh110. Michaelis-Menten curves were plotted (FIG. 3A), and $V_m$ and $K_m$ were calculated using Lineweaver-Burt plot (FIG. 3B).

To investigate the kinetics of (Rad21)2-Rh110 cleavage by Separase, Applicants incubated increasing concentrations of the substrate with 5 ng of Separase for 3 h at 37° C. Plotting the rate of (Rad21)2-Rh110 cleavage by Separase as determined by the formation of Rh110 versus the substrate concentration could be fit to the classic Michaelis-Menten hyperbola. The rate of Rh110 production at lower concentration of the substrate was proportional to the concentration of substrate, while that at higher concentration of substrate was approaching saturation (FIG. 3A). The $V_{max}$ (4.37 pmol Rh110/h, or 201 pmol Rh110/h/pmol Separase) and $K_m$ (123 µM) were calculated using a Lineweaver-Burk plot (FIG. 3B).

Example 1.3. Optimization of the Assay Conditions

Figure 4:
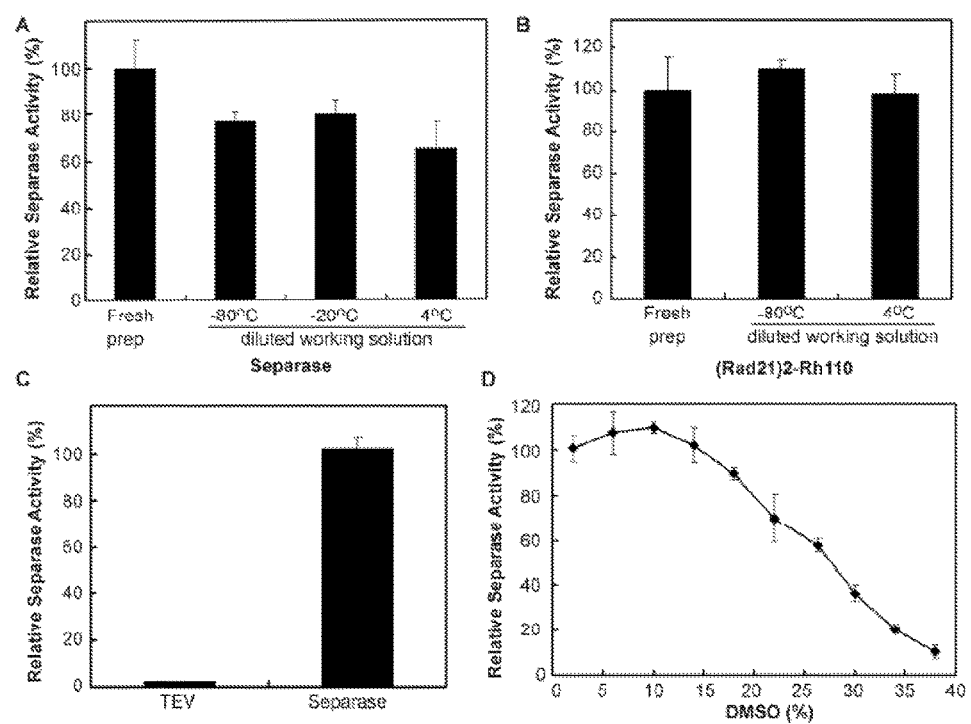
FIG. 4 shows results relating to the stability of Separase enzyme and substrate and the effect of TEV and DMSO on Separase assay.

The stability of enzyme and substrate at the working conditions is important because the process of distributing different components in high throughput screening is complicated and time-consuming. To test stability of the enzyme and substrate, Applicants diluted Separase enzyme and (Rad21)2-Rh110 to working concentration, and kept them at 4° C. for 8 h. The diluted enzyme and substrate were frozen at −20° C. or −80° C. or stored at 4° C. for 24 h before their activities were determined. The activity of Separase at the working concentration had no significant difference when it was kept at 4° C., −20° C., or −80° C. for 24 h. However, compared to the freshly prepared Separase, the activity of diluted Separase was reduced by 20% (FIG. 4A). In contrast, (Rad21)2-Rh110 at working concentration was unaffected by storage by storage at 4° C. or −80° C. for 24 h (FIG. 4B).

The construct that was used to express Separase in 293T cells contains two IgG binding domains of protein A (Z-domain), followed by four TEV-protease cleavage sequences on the N terminus of Separase (ZZ-TEV4-Separase). TEV protease was used to release the Separase from IgG-Agarose beads after activation by *Xenopus* cytostatic factor extract. To eliminate the possibility that TEV interferes with the Separase assay by cleaving (Rad21)2-Rh110, Applicants tested the activity of TEV and Separase in hydrolyzing (Rad21)2-Rh110 in parallel. The results showed that TEV could not cleave (Rad21)2-Rh110 (FIG. 4C), suggesting TEV does not interfere with the Separase assay.

Because Separase is a caspase-like protease, Applicants also tested whether caspases can cleave (Rad21)2-Rh110. Results indicated that caspase-3 and -7, two major effectors, could not cleave (Rad21)2-Rh110 (data not shown).

Figure 5:
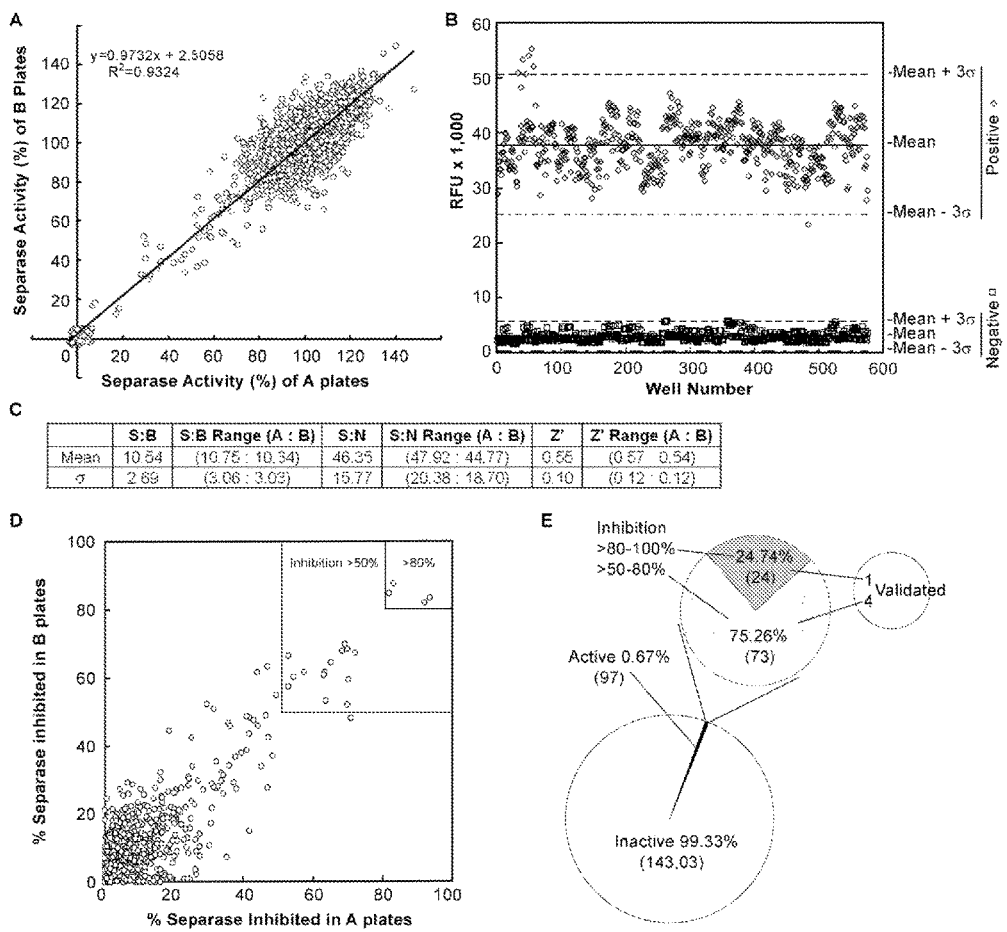
FIG. 5 shows high throughput screening for Separase inhibitors.

The stock solution of the substrate and small compounds used in high throughput screen (HTS) was prepared in DMSO. To investigate the effect of DMSO on the Separase assay, Applicants tested different concentrations of DMSO in the reaction mixture with final concentration ranging from 2% to 38%. The assay was not affected by 2-14% of DMSO, but it was inhibited with the increase of DMSO concentration of >14%. The $IC_{50}$ was ~27% (FIG. 5D). Because the DMSO concentration in Separase assay used in HTS was less than 3%, Applicants conclude that DMSO has no significant effect in this assay.

Example 1.4. High Throughput Screening for Separase Inhibitors

After two successful test runs in the HTS setting, Applicants performed screening for Separase inhibitors using the Maybridge HitFinder™ Collection that contains 14,400 compounds. Each compound was assayed in duplicate on two different plates (Plate A and Plate B). The reproducibility of the two plates could be assessed by plotting RFU of A plate versus RFU of B plate (FIG. 5A). Applicants analyzed 9 representative duplicated plates with 3,456 data points, including 288 positive controls, 288 background controls and 2,880 compound assay samples. They were highly reproducible with $R_2$=0.9324 (FIG. 5B). Except for a few data points (6 at the upper left corner and 1 at the middle right in FIG. 5B), the majority of positive controls and all background controls were within the range of mean±3σ (FIG. 5B). The overall quality of the screening was high and robust with Signal to Background ratio (S:B) 10.54, Signal to Noise ratio (S:N) 46.35 and Z' factor 0.55 (FIG. 5C). Z' factor reflects the signal dynamic range and the data variation associated with the signal measurements. The range of Z' factor is between 0 and 1. A Z' factor ≥0.5 indicates the assay was optimal.

After the percentage of Separase activity inhibited by the test compounds was calculated, those compounds that reduced Separase activity by more than 50% on both plate A and B were identified as active compounds (FIG. 5D). The majority of the compounds had very little effect on the activity of Separase, which were concentrated on the lower left corner of FIG. 5D, while a few compounds appeared on the upper right corner of FIG. 5D, inhibiting Separase activity at least by >50% (bigger square box) or by >80% (smaller square box).

Figure 9:
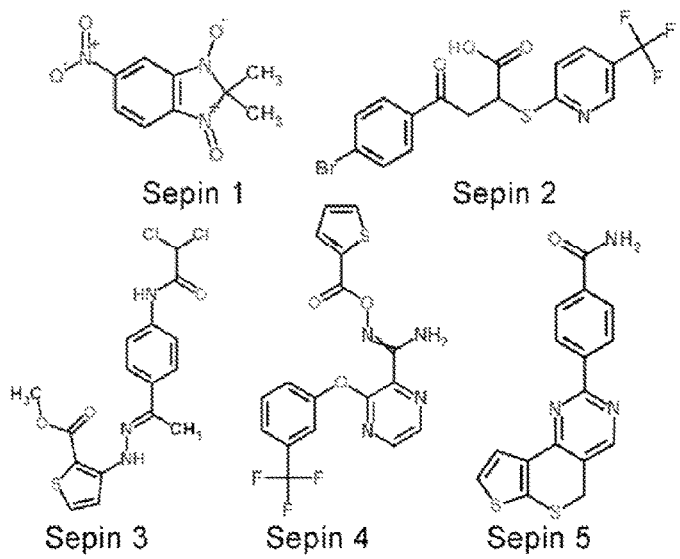
FIG. 9 provides additional data relating to the identification of leads in HTS for Separase inhibitors.
Figure 9:
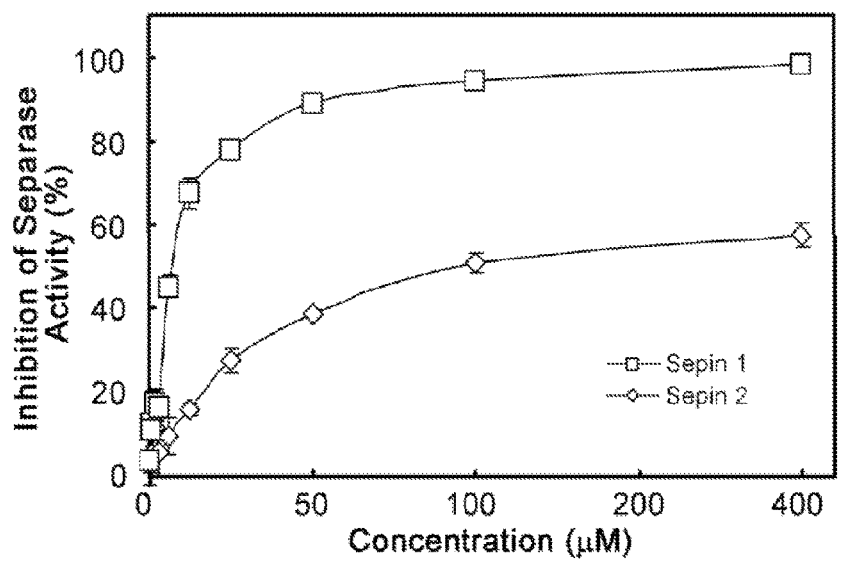

Applicants have identified 97 compounds that inhibited Separase activity by more than 50%. Among the 97 compounds, 24 reduced more than 80% of Separase activity (FIG. 5E). Applicants ordered all of these 97 compounds and verified the activities of these compounds in inhibiting Separase enzymatic activity. Five of them were confirmed, which were named Separase inhibitors (Sepin-1 to 5, shown in FIG. 9A). Among them, Sepin-1 had the highest activity, which was further characterized below. Also see FIG. 9B.

Example 1.5. Characterization of Sepin-1 in Inhibiting Separase Activity

Figure 6:
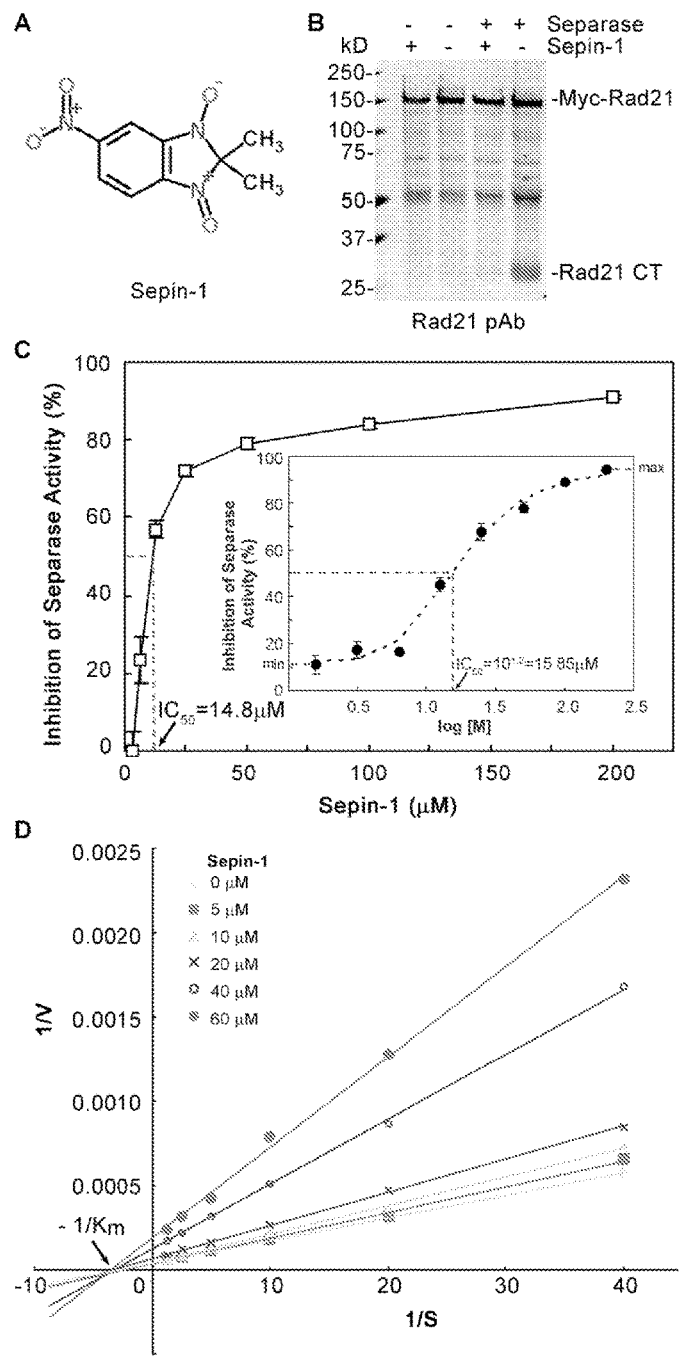
FIG. 6 provides results relating to the characterization of Sepin-1 in inhibiting Separase activity.

Sepin-1 is 2,2-dimethyl-5-nitro-2H-benzimidazole-1,3 dioxide with molecular weight 223 Da and melting point 228° C. (FIGS. 1D and 6A). Applicants used 13C NMR to confirm the identity of Sepin-1 before use for further experimentation. Sepin-1 could inhibit the Rad21 cleavage by activated Separase in vitro when in vitro transcribed and translated Rad21 was used as the substrate (FIG. 6B). In the fluorogenic Separase activity assay using (Rad21)2-Rh110 as the substrate, the concentration of Sepin-1 to inhibit 50% of Separase activity ($IC_{50}$) was 14.8 µM (FIG. 6C). To examine the kinetics of Separase inhibition by Sepin-1, different amounts of Sepin-1 compound were used to inhibit the cleavage of (Rad21)2-Rh110 by Separase. The data showed that Sepin-1 did not affect the $K_m$ but reduced the $V_{max}$ (FIG. 6D), suggesting the binding site of Sepin-1 on Separase is different from that of the substrate. To further confirm the specificity of Sepin-1 binding to Separase, 0.1% Tween-20 or 1% BSA was included in the reaction mixture. The results indicated that Tween-20 and BSA did not affect the kinetics of Sepin-1 in inhibiting Separase activity (data not shown). Based on this result Applicants conclude that the mode of Sepin-1 inhibition of Separase enzymatic activity is non-competitive. The results also indicate that Sepin-1 is not a promiscuous inhibitor.

In yeast, Separase has at least two sites interacting with Rad21. One is the catalytic site, and the other is outside the catalytic site. Although blocking the catalytic site does not affect Rad21 binding to Separase, it is unclear whether Rad21 binding to the domain outside the catalytic site has any effect on its cleavage by Separase. Non-competitive inhibition of Separase by Sepin-1 suggests that Sepin-1 might bind to a third place on Separase, which is different from the two sites that Rad21 protein binds because Sepin-1 can inhibit Separase to cleave the peptide substrate (Rad21)-Rh110 that is small and might only bind to the catalytic site of Separase.

Example 1.6. Toxicity of Sepin-1 in Mice

To investigate the toxicity in mice, Applicants injected Sepin-1 at a single dose in the range of 50-100 mg/kg body weight into C57B6 mice via tail vein. While the mice at the highest dose of 90 mg/kg died within 30-90 minutes of injection, the mice injected with a dose of <80 mg/kg had no apparent effect, and have now survived for over 6 months. Blood analysis suggested that the mice receiving 90 mg/kg of Sepin-1 had high lactate dehydrogenase (LDH) (>500 IU), suggesting muscle damage in these animals. However, the heart and skeletal muscles did not show light microscopic evidence of morphologic damage. In addition, histopathology indicated no significant lesions in major organs, including heart, lungs, liver, kidney, eye, gall bladder, pancreas, spleen, brain, adrenal gland, cervical lymph nodes, salivary gland, stomach, small intestine, skeletal muscles, bone marrow, and ear. In addition, there was no apparent distressing effect on the mice in clinical observations when the dose was 70 mg/ml or lower.

Based on the above results, Applicants expanded this study to identify the Severely Toxic Dose (i.e., dose that causes death or irreversible severe toxicity, in 10% of rodents, STD10) using more mice injected at 75 to 90 mg/Kg range. A dose of 80 mg/Kg was estimated as STD10 for Sepin-1 in these mice. When Sepin-1 was introduced to a cohort of 12 mice with a dose of 10 mg/kg via intraperitoneal injection (IP) daily for six weeks, no weight loss or apparent adverse effects on the well-being of the mice were found.

Example 1.7. Sepin-1 Inhibits the Growth of Cancer Cells and Tumors

Figure 7:
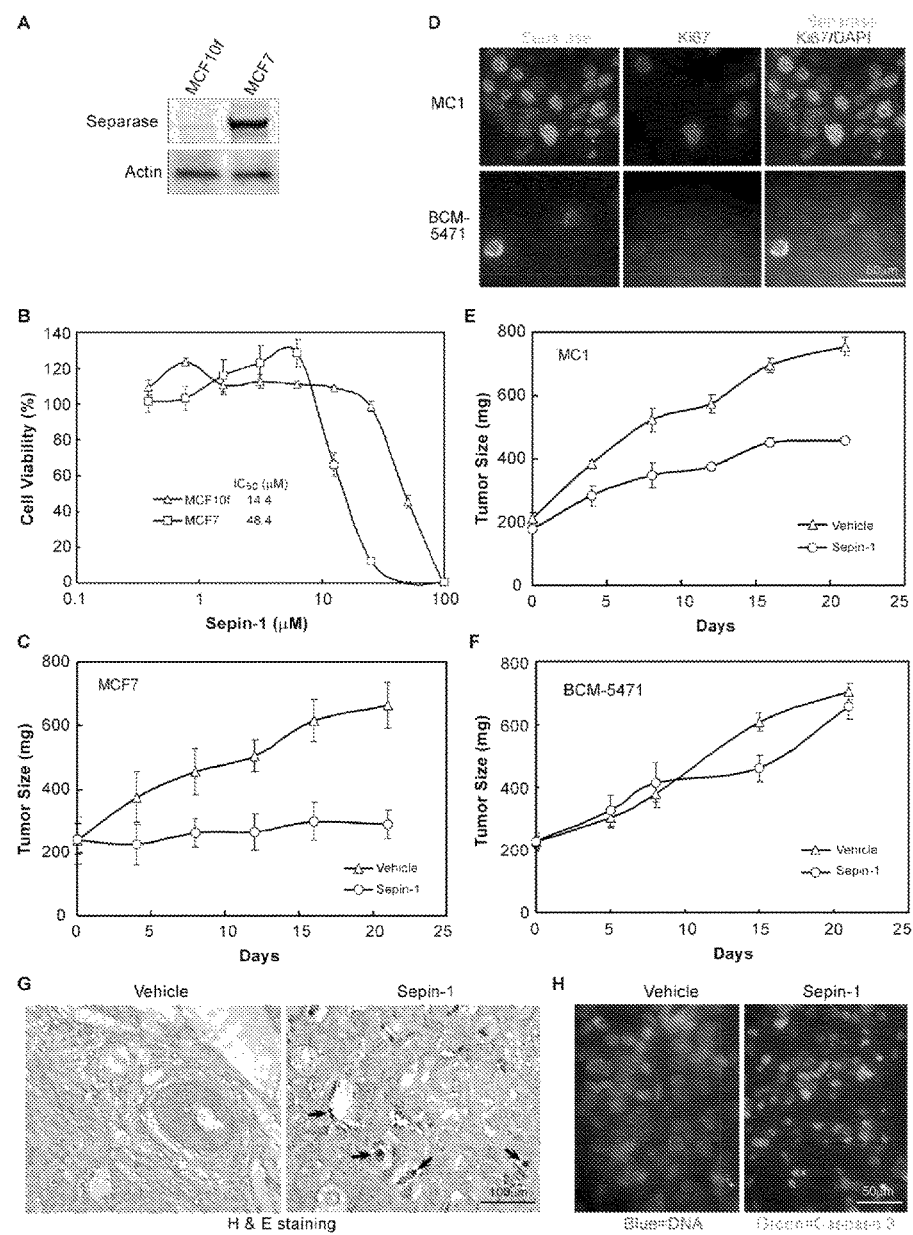
FIG. 7 shows that Sepin-1 selectively inhibits the growth of breast cancer cells and patient-derived triple negative breast cancer xenografts overexpressing Separase protein.

Based on the Sepin-1 activity in vitro, Applicants reasoned that the level of Separase in cells may affect their sensitivity to Sepin-1 (i.e., higher the Separase greater the inhibition and vice versa). To test this hypothesis, Applicants selected two breast cell lines and two tumors that have differential level of Separase protein (FIG. 7). Breast epithelial cell line MCF10f is not tumorigenic and has lower Separase level compared to isogenic MCF7 line (FIG. 7A). When treated with Sepin-1, MCF7 cells were over 3.3 times more sensitive than MCF10f cells (FIG. 7B). The sensitivity of MCF7 cells to Sepin-1 treatment was also further verified from the growth of xenograft tumors derived from MCF7 cells in mice (FIG. 7C).

Applicants also investigated Sepin-1 activity against patient derived xenografts from two triple-negative (ER– PR– HER2–) breast tumors (MC1 and BCM-5471). Compared to the BCM-5471 tumor, Separase is overexpressed in the MC1 tumor. While Separase is primarily found in the mitotic cells of the BCM-5471 tumor, in MC1 tumor it was found in majority of non-cycling (Ki67 staining negative) cells (FIG. 7D), as Applicants have previously described (Clin. Cancer Res., 2009, 15, 2703-2710. Once the tumor sizes reached ~200 mg, mice were treated with Sepin-1 at a dose of 10 mg/kg by intraperitoneal injection every day for 3 weeks. Compared to vehicle control, Sepin-1 treatment inhibited the growth of xenograft MC1 tumors by 70% over the three week treatment (FIG. 7E). However, there was no significant difference in growth between vehicle control and Sepin-1 treatment in xenograft BCM-5471 (FIG. 7F). Collectively, these data suggest that Sepin-1 inhibits tumor cell growth through selective inhibition of Separase.

Applicants used the MTT assay to test the inhibitory effect of Sepin-1 on the growth of a variety of human cancer cell lines, including leukemia, breast cancer and neuroblastoma. The results are summarized in Table 1 and FIGS. 8A-C.

TABLE 1

Half maximal inhibitory concentration (IC$_{50}$) of Sepin-1 in growth inhibition of different cancer cell lines. Cancer cells were treated with serially diluted Sepin-1 for 72 h. The cell viability was assessed using the MTT assay.

| Tumor Type | Cell lines | IC$_{50}$ (μM) | Tumor Type | Cell lines | IC50 (μM) |
|---|---|---|---|---|---|
| Leukemia | HL60 | 9.0 | Neuroblastoma | CHP212 | 9.0 |
|  | JM1 | 1.0 |  | IMR-32 | 4.8 |
|  | Jurkat | 14.0 |  | KCNR | 4.9 |
|  | Molt4 | 3.2 |  | LAN-5 | 5.0 |
|  | Raji | 4.4 |  | NGP | 7.8 |
| Breast | HBL100 | 11.5 |  | SHEP | 62.5 |
|  | MCF7 | 14.4 |  | SK-N-AS | 17.1 |
|  | MCF10F | 48.4 |  | SK-N-BE(2) | 8.6 |
|  | MDA436 | 17.8 |  | SY5Y | 4.9 |
|  | MDAMB231 | 21.5 | Brain | CHLA-02-ATRT | 7.6 |
|  | SK-BR-3 | 9.0 | Lung | A549 | 53.1 |
|  | T47D | 30.8 | Colon | HCT116 | 16.0 |
| Thyroid | TT | 33.5 |  |  |  |

Different cell lines have different sensitivity to Sepin-1 in inhibiting cell growth. The half maximal inhibitory concentration of Sepin-1 (IC$_{50}$) ranges from 1.0 μM to over 60 μM (Table 1 and FIGS. 8A-C).

Figure 8:
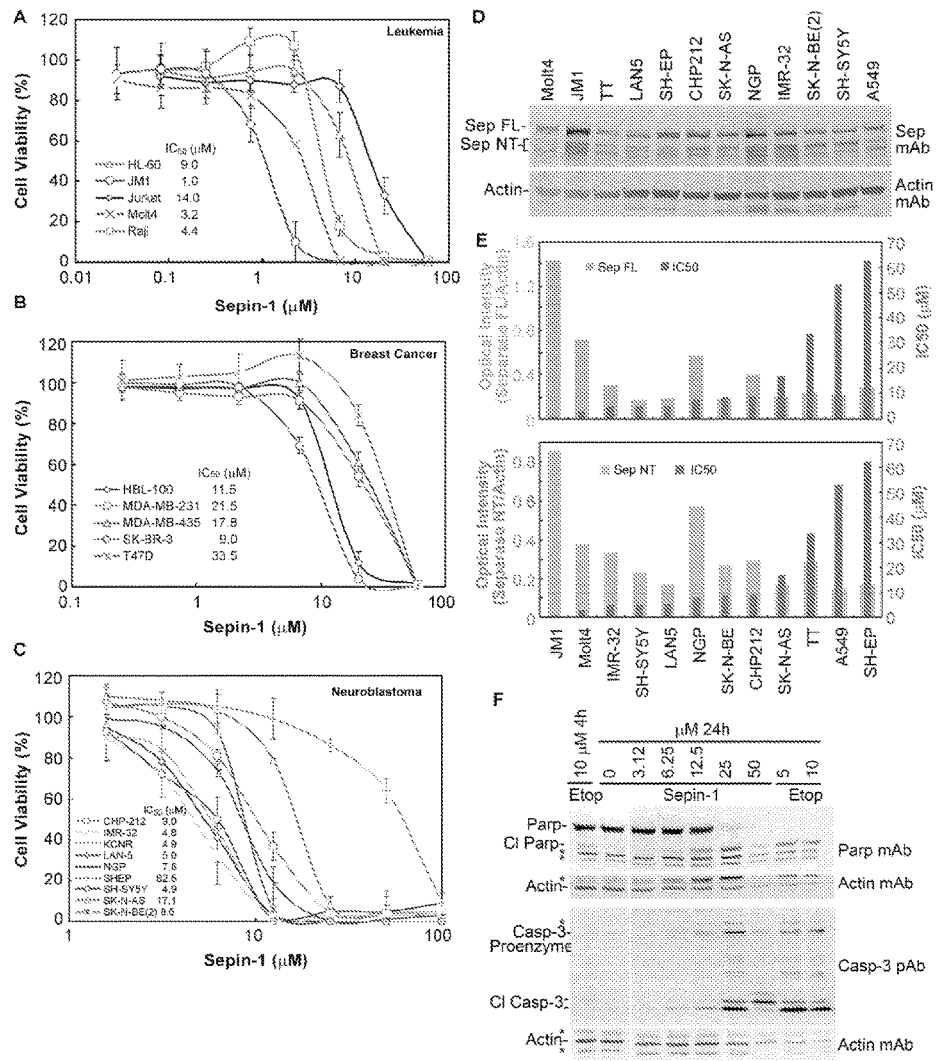
FIG. 8 shows that Sepin-1 inhibits cancer cell growth and induces apoptosis.

To define the relationship of Separase level and its sensitivity to Sepin-1 in cell lines, Applicants investigated the Separase protein level in 14 cancer cell lines (2 leukemia, 8 neuroblastoma, 1 thyroid, 1 lung cancer and 2 breast cancer cells) with Western blot (FIGS. 8D and 7A). Both full length (FL) and auto-cleaved N-terminal (NT, as a surrogate for the active protein) Separase bands were quantified and normalized with loading control protein beta actin. When IC$_{50}$ of Sepin-1 inhibiting cell growth and the Separase protein level in the particular cell line were plotted side by side, both Separase FL and NT level in cells were inversely co-related to the IC$_{50}$ values (FIG. 8E), indicating that cells overexpressing Separase are not only more sensitive to the inhibition of Separase, but may also be addicted to overexpressed Separase.

To determine the mechanism of cell growth inhibition induced by Sepin-1, Applicants performed immunoblotting to investigate if apoptosis is induced after Molt4 cells were treated with Sepin-1. Activation of caspase-3 and cleavage of poly(ADP-ribose) polymerase (Parp-1) are two commonly used parameters in determination of apoptosis. Applicants used Etoposide as a positive control, which is a well-known chemotherapy agent that induces DNA damage by interacting with topoisomerase II. Western blot data indicated that caspase-3 proenzyme was induced and activated by the formation of cleaved caspase-3 with the increase of Sepin-1 concentration. Apoptosis induction following Sepin-1 treatment was also supported by Parp-1 cleavage (FIG. 8F). In addition, Applicants observed that the effect of Sepin-1 on the activation of caspase-3 and degradation of Parp-1 is similar to that of Etoposide (FIG. 8F).

Parp-1, a chromatin-associated enzyme, catalyzes the poly ADP-ribosylation of proteins that are involved in chromatin architecture, DNA damage repair, and DNA metabolism. Parp-1 plays an important role in mediating the normal cellular response to DNA damage in non-apoptotic cells. However, it is cleaved by caspases in apoptotic cells, which is a marker of apoptosis. Although Sepin-1 induced cell growth inhibition appears to be via apoptosis, how Sepin-1 triggers the apoptosis remains to be determined.

Example 1.8. Sepin-1 Inhibits the Growth of Human Tumor Xenografts in Mice

Based on the in vitro data shown above, Applicants reasoned that Sepin-1 effect in inhibiting tumor growth in vivo is also dependent on the level of Separase (i.e. the higher the Separase level, the greater the inhibition, and vice versa). To test this hypothesis, Applicants selected two human breast cell lines (MCF7 and MCF10f) and two mammary tumors (MC1 and BCM-5471) that have differential level of Separase protein (FIG. 7). Breast epithelial cell line MCF10f is not tumorigenic and has lower Separase level compared to isogenic MCF7 line (FIG. 8A). When treated with Sepin-1, MCF7 cells were over 3.3 times more sensitive than MCF10f cells (FIG. 8B). The sensitivity of MCF7 cells to Sepin-1 treatment was also further verified from the growth of xenograft tumors derived from MCF7 cells in mice (FIG. 7C).

Applicants also investigated Sepin-1 activity against patient derived xenografts from two triple-negative (ER⁻ PR⁻ HER2⁻) breast tumors (MC1 and BCM-5471). Compared to the BCM-5471 tumor, Separase is overexpressed in the MC1 tumor (FIG. 7D). While Separase is primarily found in the mitotic cells of the BCM-5471 tumor, it was found in majority of non-cycling (Ki67 staining negative) cells in MC1 tumor (FIG. 7D), as Applicants have previously described.

Once the tumors size reached ~200 mg, mice were treated with Sepin-1 at a dose of 10 mg/kg by intraperitoneal injection every day for 3 weeks. Compared to vehicle control, Sepin-1 treatment inhibited the growth of xenograft MC1 tumors by 70% over the three week treatment (FIG. 7E). However, there was no significant difference in growth between vehicle control and Sepin-1 treatment in xenograft BCM-5471 (FIG. 7F), possibly due to low Separase level that causes less sensitivity to Sepin-1. Similar to leukemia cell line Molt4, Sepin-1-treated MFC7 xenograft tumors showed increase of apoptotic bodies in H&E stained sections (FIG. 7G), which is consistent with the finding that cleaved caspase-3 staining was significantly increased (FIG. 7H). Collectively these data suggest that Sepin-1 inhibits tumor cell growth by induction of apoptosis through selective inhibition of Separase.

In the absence of any crystal structural information, it is difficult to develop inhibitors against the Separase enzymatic active site using a rational drug design approach. HTS is an alternate approach that can be used to find potential Separase inhibitors.

Separase is an ideal drug target. Pharmacologic inhibition of Separase is a novel strategy to treat Separase overexpressed aneuploid tumors, at least because of the following reasons: 1) while homozygous deletion of Separase is embryonically lethal, mice with Separase haploinsufficiency live a normal life with no disease phenotype compared to the WT animal, indicating that reduction in Separase level has no adverse effect on an organism's wellbeing; 2) Separase, a promoter of aneuploidy, is a highly specific protease that is overexpressed in a large percentage (>60%) of human breast tumors, as well as in prostate tumors and osteosarcoma, suggesting that attenuation of Separase level pharmacologically in human cancers may kill Separase-addicted aneuploid cells; and 3) Separase is not only overexpressed but also constitutively mislocalized to the nucleus of the human tumors, providing an opportunity to target the nuclear bound Separase.

Therefore, titrating down Separase level therapeutically may not only inhibit tumor cell proliferation, but also effectively reverse the aneuploid phenotype in Separase overexpressed tumor cells, while sparing the normal cells. Furthermore, Separase mislocalization to nucleus can facilitate its targeting in the aneuploid tumor cells. Applicants also reason that cells with knockdown nuclear Separase will initiate mitotic arrest and apoptosis, and may therefore be more sensitive to traditional chemotherapy.

Example 1.9. Materials and Methods

Cell Lines

The cell lines used included leukemia: HL-60, JM1, Jurkat, Molt-4, and Raji; breast cancer: HBL100, MCF7, MCF10F, MDA-MB-436, MDA-MB-231, SK-BR-3 and T47D; thyroid cancer: TT; neuroblastoma: CHP-212, IMR-32, KCNR, LAN-5, NGP, SHEP, SK-N-AS, SK-NBE (2), and SH-SY5Y; brain tumor: CHLA-02-ATRT; lung cancer: A549; colon cancer: HCT116. The cells were cultured according to the protocols recommended by ATCC.

Antibodies

The sources of the antibodies used in this Example are as follows: Actin mAb (Sigma, St. Louis, Mo.), Parp mAb (BD Bioscience, San Jose, Calif.), Separase mAb (Abnova, Taiwan), Caspase-3 pAb (Cell Signaling technology, Danvers, Mass.), Ki67 pAb (Vector Labs, Burlingame, Calif.), Rad21 pAb (Mol. Cell Biol., 200, 22, 8267-8277).

Purification and Activation of Separase

Epitope-tagged Separase was expressed, purified and activated as described previously (Anal. Biochem., 2009, 392, 133-138).

Fluorogenic Separase Activity Assay

The substrate used in this Example is (Rad21)2-Rh110, which has two Rad21 peptide molecules (Asp-Arg-Glu-Ile-Nle-Arg) conjugated to one molecule of Rhodamine 110 (Rh110) (CPC Scientific, Sunnyvale Calif.). The assay was set up using 384-well low volume black polystyrene plates (Corning, N.Y.). Fifteen micro liter of activated Separase (~5 ng) was mixed with 5 µl of test compound. The cleavage buffer (CB) used to dilute reagents was (30 mM Hepes-KOH pH7.7, 50 mM NaCl, 25 mM NaF, 25 mM KCl, 5 mM MgCl2, 1.5 mM ATP, and 1 mM EGTA). The mixture was incubated at room temperature for 1 h, and then 5 µl of 0.2 mM substrate (Rad21)2-Rh110 was added. The positive control contained Separase, substrate and CB without the test compound. The negative control contained substrate and CB only. After the reaction mixture was incubated at 37° C. for 3 h, the relative fluorescence intensity was measured (without stopping the enzymatic activity) at $\lambda_{ex}$=390 nm/$\lambda_{em}$=450 nm for 7-amido-4-methyl coumaric acid (AMC) released from Rad21-MCA or $\lambda_{ex}$=490 nm/$\lambda_{em}$=528 nm for Rh110 released from (Rad21)2-Rh110 using a Synergy™ 4 Multi-Mode Microplate Reader (BioTek Instruments Inc., Winooski, Vt.).

High Throughput Screening (HTS)

HTS was performed at the John S. Dunn Gulf Coast Consortium for Chemical Genomics at the University of Texas Medical School at Houston. The compound library used in HTS was the Maybridge HitFinder™ Collection that contains 14,400 compounds. The compounds were stored in 180 96-well plates, 80 compounds per plate. The concentration of the stock solution of each compound was 10 mM in DMSO. Each compound was diluted to 500 µM in CB using a Biomek FX automation workstation (Beckman Coulter, Inc. Brea, Calif.) immediately before the assay was performed. HTS was performed on 384-well plates using a Biomek NX Automation Workstation (Beckman Coulter, Inc.) to dispense the compounds and Separase enzyme. Three hundred and twenty compounds were assayed in every 384-well plate. In each assay well, 5 µl of 500 µM compound was mixed with 5 ng of Separase in 15 µl CB. The reaction mixture was incubated at 25° C. for 1 h. After 5 µl of substrate was added to the reaction mixture using Thermo Scientific Multidrop Combi Reagent Dispenser (Thermo Fisher Scientific, Waltham Mass.), the plate was incubated at 37° C. for 3 h. Each assay plate included 32 positive controls in which CB was used instead of the compounds, and 32 negative controls which did not have either compound or Separase. Each compound was assayed in duplicate in two separate plates (A and B). The RFI was determined with Tecan Infinite 200 Reader (Tecan Group Ltd, Switzerland). The quality of HTS was evaluated by Signal to Background ratio (S:B), Signal to Noise ratio (S:N), and Z' defined as S:B=RFIpositive/RFInegative, S:N=(RFIpositive−RFInegative)/STDEVnegative, and Z'=1−[(3*STDEVpositive+3*STDEVnegative)/(RFIpositive−RFInegative)]. The percent inhibition of Separase enzyme activity by compounds was calculated as 100*{1−[(RFIcompound−RFInegative)/(RFIpositive−RFInegative)]}. The compounds that inhibited more than 50% of Separase activity on both plate A and B were identified as hits.

In Vitro Cytotoxicity Assay

The inhibitory effect of Sepin-1 on cell growth was assayed using the 3-(4,5-dimethylthiazol-2yl)-2,5-diphenyl-tetrazolium bromide (MTT) colorimetric dye reduction method (Cancer Chemother. Pharmacol., 2006, 58, 13-23). One hundred thirty-five µl of exponentially growing cancer cells were plated at a density of $0.4-1.0 \times 10^5$ cells/well in a 96-well microtiter plate. After 16 h, Sepin-1 at specified concentrations was added to each well. After 72 h of continuous drug exposure, 15 µl of 5 mg/ml MTT was added to each well and the plates were incubated for 4 h at 37° C. Medium was replaced with 150 µl of DMSO to solubilize the formazan, and the optical density (OD) was measured at 550 nm using a microplate spectrophotometer (Anthos Analytical, Durham, N.C., USA). Cell viability was calculated by subtracting the background OD of media alone from the OD of test wells, then dividing by the OD of the control (untreated) wells. Replicates of 3 wells were used for each drug concentration. The in vitro cytotoxicity assay was repeated once and the $IC_{50}$ reported was the average of two independent experiments.

Toxicity of Sepin-1 in Mice

To test Maximum Tolerated Dose (MTD) and No Observable Effect Level (NOEL) of Sepin-1, Applicants applied 200 µl Sepin-1 (diluted in PBS) one time at an acute dose range of 50 to 100 mg/kg body weight to 8-10 weeks old C57B6 mice (~25 g) through intravenous tail vein injection (n=3/group). Except for the MTD dose, after Sepin-1 injection, the mice were returned to the cage and their reaction to the drug was monitored from one week to several months. Complete necropsy, blood chemistry and pathology of the Sepin-1 injected mice were carried out by the Comparative Pathology Laboratory at the Baylor College of Medicine.

Growth Inhibition of Xenograft Tumors

Patient-derived xenograft (PDX) lines MC1 (ER− PR− HER2−) (Proc Natl Acad Sci USA. 100, 2003, 3983-3988) and BCM-5471 (ER− PR− HER2−) (Cancer Res. 73, 2013, 4885-4897) were maintained as described (Cancer Res. 73, 2013, 4885-4897) by serial transplantation into SCID Beige immunocompromised host mice whose endogenous mammary epithelium was removed surgically (Cancer Res. 19, 1959, 515-20).

For treatment studies, MCF7 xenografts (ER+ PR+ HER2−) were generated by injection of one million cultured cells grown under standard in vitro conditions as previously described (Proc. Natl. Acad. Sci. U. S. A 105, 2008, 13033-13038). Donor tumors for PDX lines MC1 and BCM-5471 were divided into small fragments and retransplanted into the fat pat of recipient SCID Beige mice (5 mice per group). When the tumors reached approximately ~200 mg, mice were treated with either vehicle or Sepin-1. Sepin-1 was injected at dose of 10 mg/kg daily for 5 days a week for 3 weeks. Guided by toxicity studies, Applicants chose this dose for SCID-beige mice with no apparent effect on body weight. Vehicle injected mice served as controls. Size of the xenografts were measured every four days using calipers and tumor weight was estimated using the guidelines by NCI for xenograft evaluation (http://ncifrederick.cancer.gov/Lasp/Acuc/Frederick/Media/Documents/ACUC14.pdf).

After 3 weeks treatment, the tumors were harvested and fixed in 10% Buffed Formalin Phosphate (Fisher Scientific, Pittsburgh, Pa.) overnight. The tumor tissues were washed with PBS for 3×30 min; dehydrated for 1 h at 70%, 80%, 90% and 100% two times; and immerged in Xylene several times until the tissues became clear. The samples were embedded in wax and sectioned with 5 µm in thickness. All mice were maintained in accordance with the NIH Guide for the Care and Use of Laboratory Animals with approval from the Baylor College of Medicine Institutional Animal Care and Use Committee.

In Vitro Cleavage of Myc-Rad21 Assay

Myc-Rad21 protein was prepared by using pCS2MT Rad21 plasmid (Cancer Res., 1959, 19, 515-520) as the template and the TNT SP6 High-Yield Wheat Germ Protein Expression kit (Promega, Madison, Wis.). Myc-Rad21 protein was mixed with Separase with or without the presence of Sepin-1. The final concentration of Sepin-1 was 50 µM. The reaction mixture was incubated in a 37° C. water bath for 1 h. The cleavage of myc-Rad21 was immunoblotted with Rad21 pAb.

Characterization of Sepin-1 Mediated Inhibition of Separase Activity In Vitro

Different amounts of Sepin-1 were mixed with activated Separase for 30 min before substrate $(Rad21)_2$-Rh110 was added. After 3 h incubation at 37° C., the fluorescence intensity of Rh110 was determined. $IC_{50}$ was calculated using either KaleidaGraph program (Synerge software, Reading, Pa.) or four parameter logistic equation (4-parameter dose-response curve fit): Inhibition of Activity $(\%) = \min + (\max - \min) / \{1 + (\log [M]/IC_{50})\}^{Hill\ Slop}$, where "min" and "max" represent minimal and maximal activity inhibition, respectively. Hill Slop is the slope of the curve at its midpoint. To identify the mode of Sepin-1 interacting with Separase, different amounts of both Sepin-1 and (Rad21)2-Rh110 were used in the Separase activity assay.

Immunofluorescence Microscopy

Deparafinization of tumor tissue sections and immunostaining were performed using the protocol reported previously (Clin. Cancer Res., 2009, 15, 2703-2710).

Immunoblotting

Preparation of protein samples and Western blot were performed as described previously (J Cell Biol, 2008, 183, 1019-1031; PLoS. ONE., 2013, 8, e69458).

pictures of normal brain (bottom panel) and a pediatric glioblastoma samples (#4687, top panel) showing Separase expression and nuclear localization in non-mitotic GBM cells but not in normal brain. FIG. 10B shows Kaplan-Meier plot showing significantly lower survival in GBM patients with high Separase expression (n=12). FIG. 10C provides MTT cytotoxicity assays showing efficient cell death of two Separase overexpressing primary pediatric glioblastoma samples. The inset (Western blot) shows levels of Separase in these samples. FIG. 10D provides survival analysis show-

TABLE 2

Summary of robustness of the HTS for Separase inhibitors.

| Screening Plate No.[a] | Compound Plate No.[b] | Signal:Bacground (S:B) | S:B Range (A:B)[c] | Signal:Noise (S:N) | S:N Range (A:B) | Z' | Z' Range (A:B) |
|---|---|---|---|---|---|---|---|
| 1 | 1-4 | 7.45 | (7.7:7.2) | 38.26 | (36.6:39.9) | 0.34 | (0.37:0.31) |
| 2 | 5-8 | 8.15 | (8.5:7.8) | 45.87 | (44.4:47.3) | 0.66 | (0.66:0.67) |
| 3 | 9-12 | 5.93 | (5.1:6.7) | 34.77 | (24.6:44.9) | 0.48 | (0.39:0.56) |
| 4 | 13-16 | 5.27 | (5.0:5.5) | 18.48 | (16.8:20.1) | 0.37 | (0.38:0.36) |
| 5 | 17-20 | 6.99 | (8.3:5.7) | 29.47 | (38.3:20.7) | 0.53 | (0.64:0.42) |
| 6 | 21-24 | 6.55 | (7.5:5.6) | 38.71 | (43.4:34.0) | 0.60 | (0.71:0.48) |
| 7 | 25-28 | 8.23 | (9.0:7.5) | 49.41 | (52.3:46.5) | 0.58 | (0.58:0.58) |
| 8 | 29-32 | 6.19 | (5.2:7.1) | 21.36 | (16.4:26.3) | 0.39 | (0.35:0.44) |
| 9 | 33-36 | 6.65 | (7.6:5.7) | 21.30 | (26.4:16.2) | 0.51 | (0.55:0.47) |
| 10 | 37-40 | 6.12 | (5.9:6.4) | 49.93 | (50.8:49.1) | 0.54 | (0.62:0.46) |
| 11 | 41-44 | 14.37 | (14.3:14.5) | 42.77 | (42.7:42.8) | 0.47 | (0.66:0.47) |
| 12 | 45-48 | 13.19 | (14.2:12.2) | 50.17 | (61.5:38.8) | 0.66 | (0.66:0.65) |
| 13 | 49-52 | 13.44 | (14.9:12.0) | 53.44 | (62.1:44.7) | 0.67 | (0.69:0.64) |
| 14 | 53-56 | 13.31 | (11.9:14.8) | 51.51 | (38.5:64.5) | 0.71 | (0.67:0.75) |
| 15 | 57-60 | 12.58 | (11.5:13.7) | 44.35 | (41.5:47.2) | 0.69 | (0.65:0.74) |
| 16 | 61-64 | 12.00 | (14.0:10.0) | 41.44 | (51.0:31.9) | 0.69 | (0.69:0.68) |
| 17 | 65-68 | 13.45 | (14.1:12.8) | 70.20 | (41.5:98.9) | 0.70 | (0.70:0.70) |
| 18 | 69-72 | 13.46 | (12.9:14.0) | 48.11 | (47.1:49.1) | 0.66 | (0.64:0.67) |
| 19 | 73-76 | 12.00 | (11.7:12.3) | 40.58 | (36.8:44.4) | 0.57 | (0.57:0.57) |
| 20 | 77-80 | 7.08 | (7.4:6.8) | 31.82 | (35.8:27.8) | 0.40 | (0.42:0.38) |
| 21 | 81-84 | 11.74 | (12.6:10.8) | 59.46 | (75.4:43.5) | 0.51 | (0.63:0.51) |
| 22 | 85-88 | 8.91 | (10.6:7.3) | 29.09 | (32.5:25.7) | 0.53 | (0.63:0.44) |
| 23 | 89-92 | 14.58 | (16.1:13.1) | 79.42 | (113.6:45.3) | 0.66 | (0.70:0.62) |
| 24 | 93-96 | 9.45 | (11.4:7.5) | 26.56 | (35.2:17.9) | 0.47 | (0.51:0.43) |
| 25 | 97-100 | 10.12 | (12.3:8.0) | 38.91 | (49.1:28.7) | 0.37 | (0.53:0.22) |
| 26 | 101-104 | 12.77 | (12.3:13.3) | 59.57 | (53.0:66.1) | 0.61 | (0.56:0.65) |
| 27 | 105-108 | 11.00 | (9.6:12.4) | 55.56 | (54.5:56.6) | 0.65 | (0.67:0.64) |
| 28 | 109-112 | 12.98 | (14.8:11.1) | 50.40 | (63.6:37.2) | 0.68 | (0.72:0.64) |
| 29 | 113-116 | 11.58 | (9.0:14.1) | 44.27 | (37.6:51.0) | 0.66 | (0.68:0.64) |
| 30 | 117-120 | 13.77 | (15.3:12.2) | 85.18 | (101.6:68.8) | 0.68 | (0.71:0.65) |
| 31 | 121-124 | 13.13 | (11.9:14.4) | 79.12 | (74.0:84.3) | 0.59 | (0.59:0.60) |
| 32 | 125-128 | 10.59 | (8.2:13.0) | 46.81 | (24.3:69.3) | 0.40 | (0.34:0.46) |
| 33 | 129-132 | 12.55 | (9.9:15.2) | 66.61 | (43.9:89.3) | 0.44 | (0.34:0.53) |
| 34 | 133-136 | 11.52 | (12.8:10.3) | 51.14 | (64.6:37.7) | 0.60 | (0.57:0.62) |
| 35 | 137-140 | 8.12 | (6.9:9.4) | 45.53 | (59.9:31.1) | 0.55 | (0.57:0.54) |
| 36 | 141-144 | 13.82 | (15.7:11.9) | 58.34 | (63.6:53.1) | 0.58 | (0.62:0.54) |
| 37 | 145-148 | 8.55 | (9.2:7.9) | 21.05 | (23.6:18.5) | 0.49 | (0.48:0.50) |
| 38 | 149-152 | 10.55 | (10.1:11.0) | 44.29 | (46.6:41.9) | 0.59 | (0.59:0.60) |
| 39 | 153-156 | 9.97 | (7.9:12.1) | 31.56 | (26.3:36.8) | 0.44 | (0.33:0.56) |
| 40 | 157-160 | 8.91 | (10.6:7.3) | 29.09 | (32.5:25.7) | 0.53 | (0.63:0.44) |
| 41 | 161-164 | 11.04 | (10.2:11.9) | 54.27 | (39.6:68.9) | 0.53 | (0.45:0.60) |
| 42 | 165-168 | 13.38 | (14.9:11.9) | 62.31 | (65.3:59.3) | 0.59 | (0.68:0.50) |
| 43 | 169-172 | 9.87 | (12.6:7.2) | 61.59 | (79.8:43.4) | 0.49 | (0.60:0.38) |
| 44 | 173-176 | 11.86 | (9.6:14.1) | 32.04 | (24.5:39.5) | 0.46 | (0.40:0.52) |
| 45 | 177-180 | 11.02 | (12.4:9.7) | 51.57 | (63.3:39.8) | 0.51 | (0.53:0.49) |
| Average | | 10.54 | (10.75: | 46.35 | (47.92:44.77) | 0.55 | (0.57:0.54) |
| SD | | 2.69 | (3.06:3.03) | 15.77 | (20.38:18.70) | 0.10 | (0.12:0.12) |

[a]384-well plates were used for the HTS.
[b]Aliquots of compound stocks were in 96-well plates, 80 compounds/plate. Compounds from every 4 plates were screened in one 384-well plate.
[c]The screening was duplicated. Two duplicated 384-well plates were named A and B, respectively.

Example 2. Inhibition of the Growth of Glioblastoma Cells by Sepin-1

Figure 10:
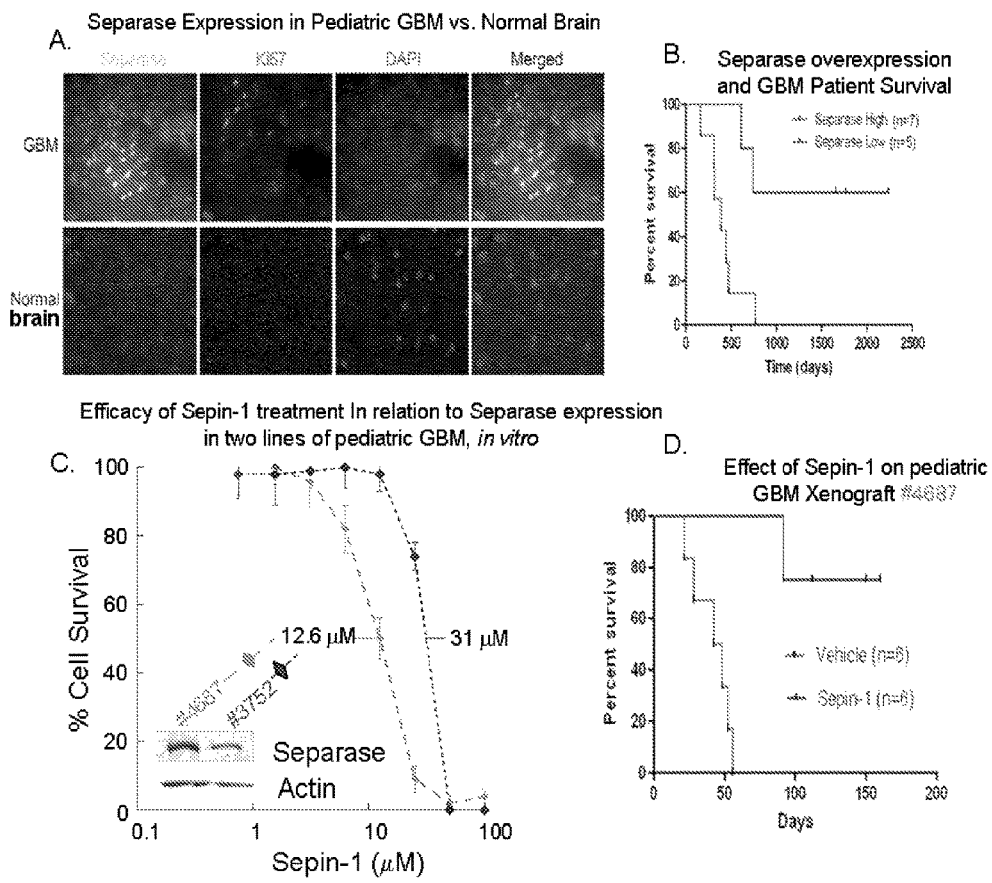
FIG. 10 provides data relating to separase overexpression in Pediatric glioblastoma (GBM) and the effect of Sepin-1 in inhibiting the growth of glioblastoma cells in vitro and in vivo.

FIG. 10 provides data relating to separase overexpression in Pediatric glioblastoma (GBM) and the effect of Sepin-1 in inhibiting the growth of glioblastoma cells in vitro and in vivo. FIG. 10A shows representative immunofluorescence ing a significant increase in the life span of Sepin-1 treated mice with orthotopic xenograft of Separase overexpressing pediatric GBM tumor (#4687). SCID-beige mice after two weeks of transplantation were treated at a dose of 10 mg/kg daily ip for 5 days a week for 4 weeks with either Sepin-1 or vehicle (n=6/group).

Example 3. Optimization of Sepin-1

Figure 11:
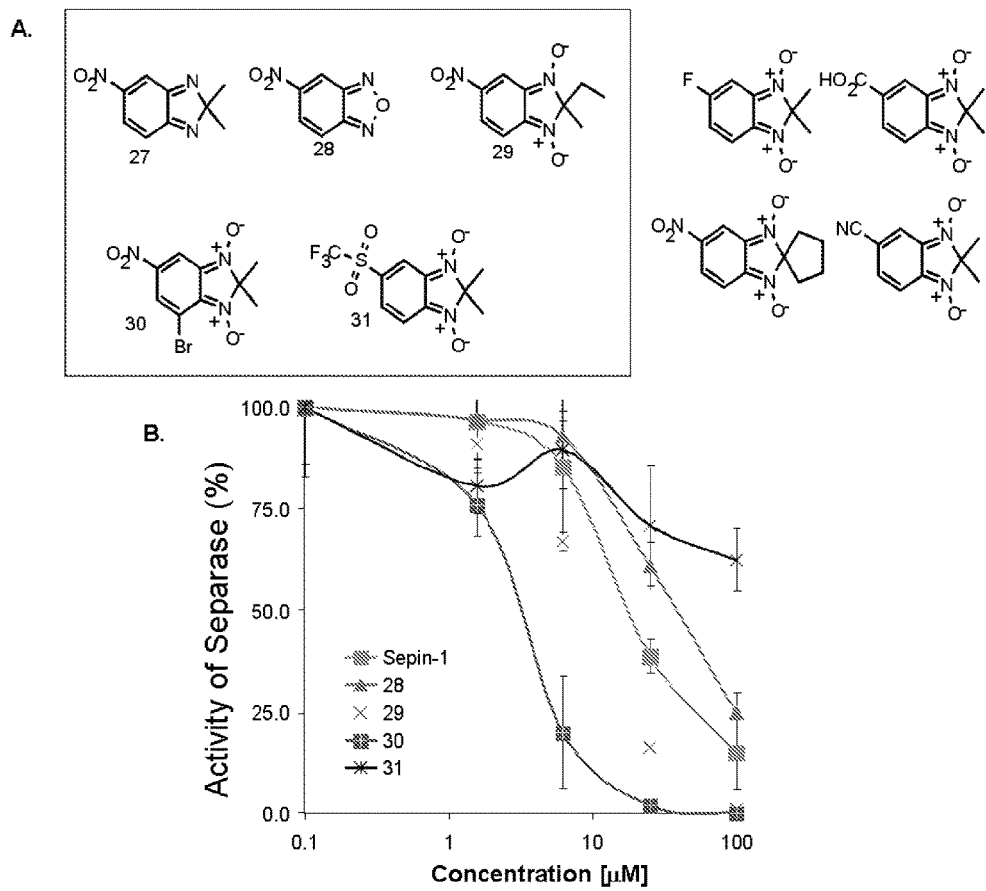
FIG. 11 provides additional data relating to structure-activity studies of Sepin-1 derivatives.

This Example pertains to the optimization of the structure of Sepin-1 to obtain Sepin-1 analogs with higher potency. Over 30 sepin-1 derivatives were synthesized and tested. FIG. 11A illustrates the Sepin-1 derivatives that were synthesized and examined. The separase activity of the Sepin-1 derivatives shown in the box in FIG. 11A (compounds 27-31) were tested. The results are summarized in FIG. 11B.

As shown in FIG. 11B, Applicants observed that compound 29 was approximately twice as active as lead compound 27. Applicants also observed that compound 30 was approximately 10 times more active than lead compound 27.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A composition for inhibiting Separase activity, wherein the composition comprises a compound selected from the group consisting of:

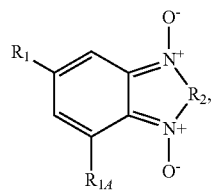

wherein $R_1$ is $NO_2$, $R_{1A}$ is Br, and $R_2$ is $C(CH_3)_2$;

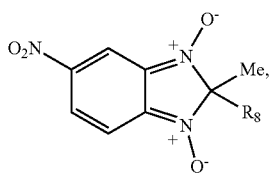

wherein $R_8$ is selected from the group consisting of an alkane, $CH_3$, $CH_2CH_3$, a cycloalkane, cyclopentane, cyclohexane, a phenyl group, $C_4H_9$, CO, and CS;

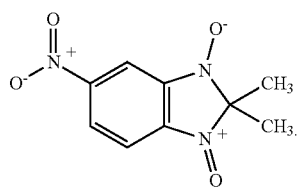

and combinations thereof.

2. The compositions of claim 1, wherein the compound is water soluble.

3. The composition of claim 1, wherein the compound is a selective inhibitor of Separase.

4. The composition of claim 1, wherein the compound is a non-competitive inhibitor of Separase.

5. A method of treating a tumor in a subject, wherein the method comprises:
administering a composition to the subject, wherein the composition comprises a compound that inhibits Separase activity,
wherein the compound is selected from the group consisting of:

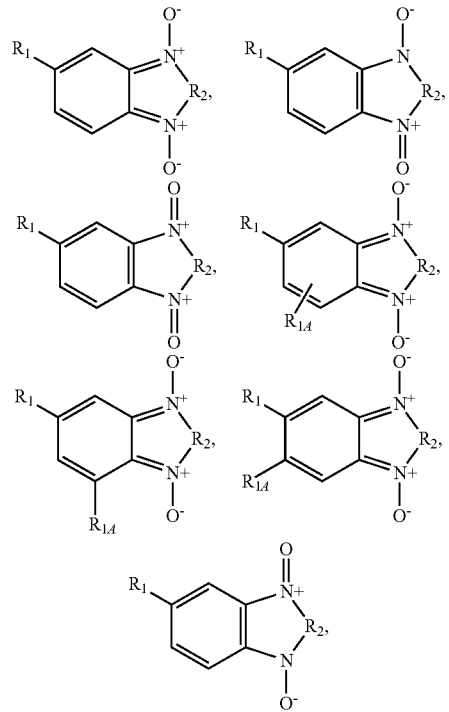

and combinations thereof, wherein $R_1$ and $R_{1A}$ are each selected from the group consisting of an alkane, an alkene, an alkyne, a carboxyl group, an alkoxy group, a methoxy group, an ether, a nitro group, a nitrile, sulfate, a sulfonate, a halogen, a primary amine group, a secondary amine group, a tertiary amine group, an alcohol, a boronic acid, a triazole, a photo-reactive group, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, a phenyl group, $CH_2$-phenyl, and $SO_3H$, wherein $R_3$ is selected from the group consisting of H, OH, $CH_3$, $C_4H_9$, and an alkyl group, wherein $R_2$ is selected from the group consisting of an alkane, $C(CH_3)_2$, a cycloalkane, a cyclopentane, a cyclohexane, a phenyl group, $C(R_7)(R_{7.5})$, $C(CH_3)(R_{7.5})$, $C(CH_3)(CH_2CH_3)$, $C(CH_3)(Phenyl)$, $C(CH_3)(CF_3)$, $C(C_4H_9)_2$, CO, CS, and $CH_2$, O, and wherein $R_7$ and $R_{7.5}$ are each selected from the group consisting of an alkane, $CH_3$, $CH_2CH_3$, a cycloalkane, cyclopentane, cyclohexane, a phenyl group, $C_4H_9$, CO, and CS; and wherein the tumor is associated with at least one of breast cancer, leukemia, thyroid cancer, neuroblastoma, brain cancer, lung cancer, colon cancer, prostate cancer, osteosarcoma, glioblastoma, and combinations thereof.

6. The method of claim 5, wherein the tumor comprises Separase overexpressed tumor cells.

7. The method of claim 5, wherein the tumor comprises Separase overexpressed mammary tumor cells.

8. The method of claim 5, wherein the tumor comprises Separase overexpressed aneuploid cells.

9. The method of claim 5, wherein the tumor is associated with breast cancer.

10. The method of claim 5, wherein the subject is a human being.

11. The method of claim 5, wherein the subject is a human being suffering from cancer, and wherein the cancer is selected from the group consisting of leukemia, breast cancer, thyroid cancer, neuroblastoma, glioblastoma, brain cancer, lung cancer, colon cancer, prostate cancer, osteosarcoma, and combinations thereof.

12. The method of claim 5, wherein the administering of the composition comprises intravenous administration.

13. The method of claim 5, wherein the compound is a selective inhibitor of Separase.

14. The method of claim 5, wherein the compound is a non-competitive inhibitor of Separase.

15. The method of claim 5, wherein the compound selectively inhibits growth of Separase overexpressed tumor cells associated with the tumor.

16. The method of claim 5, wherein the compound comprises the following structure:

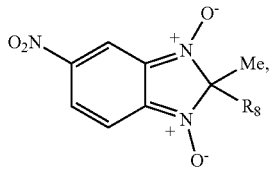

wherein $R_8$ is selected from the group consisting of an alkane, $CH_3$, $CH_2CH_3$, a cycloalkane, cyclopentane, cyclohexane, a phenyl group, $C_4H_9$, CO, and CS.

17. The method of claim 5, wherein the compound comprises the following structure:

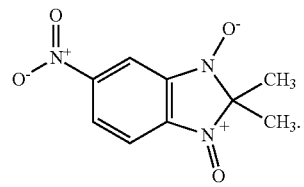

18. The method of claim 5, wherein the compound comprises the following structure:

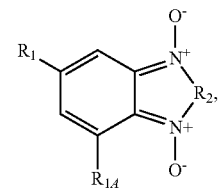

wherein $R_1$ and $R_{14}$ are each selected from the group consisting of an alkane, an alkene, an alkyne, a carboxyl group, an alkoxy group, a methoxy group, an ether, a nitro group, a nitrile, sulfate, a sulfonate, a halogen, a primary amine group, a secondary amine group, a tertiary amine group, an alcohol, a boronic acid, a triazole, a photo-reactive group, OH, $NH_2$, $NO_2$, Br, F, Cl, I, $CF_3$, $CF_3SO_2$, $C(N_2)CF_3$, CN, $CH_3$, $CH_3O$, $CO_2H$, $CONH_2$, $CONHR_3$, $NHR_3$, $N(R_3)_2$, $C_2R_3$, $C_4H_9$, a phenyl group, $CH_2$-phenyl, and $SO_3H$;

wherein $R_3$ is selected from the group consisting of H, OH, $CH_3$, $C_4H_9$, and an alkyl group;

wherein $R_2$ is selected from the group consisting of an alkane, $C(CH_3)_2$, a cycloalkane, cyclopentane, cyclohexane, a phenyl group, $C(R_7)(R_{7.5})$, $C(CH_3)(R_{7.5})$, $C(CH_3)(CH_2CH_3)$, $C(CH_3)(Phenyl)$, $C(CH_3)(CF_3)$, $C(C_4H_9)_2$, CO, CS, $CH_2$, and O; and wherein $R_7$ and $R_{7.5}$ are each selected from the group consisting of an alkane, $CH_3$, $CH_2CH_3$, a cycloalkane, cyclopentane, cyclohexane, a phenyl group, $C_4H_9$, CO, and CS.

19. The method of claim 18, wherein $R_1$ is $NO_2$, $R_{14}$ is Br, and $R_2$ is $C(CH_3)_2$.

* * * * *